United States Patent [19]

Taddei-Peters et al.

[11] Patent Number: 5,874,544
[45] Date of Patent: Feb. 23, 1999

[54] ANTIBODIES TO APO(A)

[75] Inventors: W. C. Taddei-Peters, Gaithersburg; Sandra M. Butler, Laurel, both of Md.

[73] Assignee: Perimmune Holdings, Inc., Rockville, Md.

[21] Appl. No.: 892,544

[22] Filed: Jul. 14, 1997

Related U.S. Application Data

[62] Division of Ser. No. 457,449, Jun. 1, 1995, Pat. No. 5,708,138, which is a division of Ser. No. 266,407, Jun. 27, 1994, Pat. No. 5,786,156, which is a continuation-in-part of Ser. No. 172,461, Dec. 21, 1993, abandoned.

[51] Int. Cl.⁶ .................................................. C07K 16/18
[52] U.S. Cl. ................................. 530/387.9; 530/388.25; 530/389.3
[58] Field of Search .............................. 530/387.9, 388.1, 530/388.25, 389.3

[56] References Cited

U.S. PATENT DOCUMENTS

| | | |
|---|---|---|
| 4,677,057 | 6/1987 | Curtiss et al. . |
| 4,945,040 | 7/1990 | Fless et al. . |
| 4,970,144 | 11/1990 | Fareed et al. . |
| 5,055,396 | 10/1991 | Curtiss et al. . |
| 5,126,240 | 6/1992 | Curtiss et al. . |
| 5,206,086 | 4/1993 | Sparks et al. . |

FOREIGN PATENT DOCUMENTS

| | | |
|---|---|---|
| WO 9209893 | 6/1992 | WIPO . |
| WO 9221015 | 11/1992 | WIPO . |

OTHER PUBLICATIONS

Koritnick DL and Rudel LL, J Lipid Res, 24:1639–1645, 1983.

Harlow E and Lane D, Antibodies: a Laboratory Manual, Cold Spring Harbor Laboratory, p. 76, 1988.

Lerner RA, Nature, 299:593–596, Oct. 1982.

Guo HC, Arteriosclerosis and Thrombosis, 11:1030–1041, 1991.

W.L.T. Wong et al., "A Monoclonal–Antibody–Based Enzyme–Linked Immunoabsorbent Assay of Lipoprotein(a)," Clin. Chem., 36/2, 192–197 (1990).

C. Lauber et al., "Lipoprotein(a) Quantified by an Enzyme–Linked Immuno–Absorbent Assay with Monoclonal Antibodies," Clin Chem, 35/7, 1380–1384, 1989.

J.P. van Biervilet et al., "Lipoprotein(a) profiles and evolution in newborns" Atherosclerosis, 86 (1991), 173–181.

C. Lackner et al., "Molecular Basis of Apolipoprotein (a) Isoform Heterogenity as Revealed by Pulsed–Field Gel Electrophoresis," J. Clin. Invest., vol. 87, Jun. 1991, pp. 2153–2161, USA.

M.I. Kamboh et al., "Expressed Hypervariable Polymorphism of Apolipoprotein (a)," Am. J. Hum. Genet., 49:1063–1074, 1991, USA.

S.M. Marcovina, "Identification of 34 Apolipoprotein(a) Isoforms: Differential Expression of Apolipoprotein(a) Alleles Between American Blacks and Whites," Biochemical and Biophysical Research Communication, vol. 191, No. 3, pp. 1192–1196, Mar. 31, 1993, USA.

G. Utermann et al., "Lp(a) Glycoprotein Phenotypes," J. Clin. Invest., vol. 80, Aug. 1987, pp. 458–465, USA.

C. Sandholzer et al.,"Apo(a) Isoforms Predict Risk for Coronary Heart Disease" Arteriosclerosis and Thrombosis, vol. 12, No. 10, Oct. 1992 pp. 1214–1226.

S. Marcovina et al., "Lipoprotein(a) Concentrations and Apolipoprotein(a) Phenotypes in Caucasians and African Americans," Arteriosclerosis and Thrombosis, vol. 13, No. 7, Jul. 1993, pp. 1037–1045.

J. Gaubatz et al., "Polymorphic forms of human apolipoprotein(a): inheritance and relationship of their molecular weights to plasma levels of lipoprotein(a)," Journal of Lipid Research, vol. 31, pp. 603–613, 1990.

D.Rainwater et al., "Immunochemical characterization of lipoprotein(a) in baboons" Atherosclerosis, vol. 73, pp. 23–31, 1988, Ireland.

B. Butman et al., "Monoclonal Antibodies Which Identify a Genus–Specific Listeria Antigen," Applied and Environmental Microbiology, vol. 54, No. 6, pp. 1564–1569, Jun. 1988, USA.

H. Schagger et al., "Tricine–Sodium Dodecyl Sulfate–Polyacrylamide Gel Electrophoresis for the Separation of Proteins in the Range from about 1 to 100 KDa", Analytical Biochemistry, vol. 166, pp. 368–379 (1987).

B.R. Clark et al., "Enzyme–Liquid Immunosorbent Assay (ELISA): Theoretical and Practical Aspects" Immunoenzyme Techniques, E.T. Maggio, ed., CRC Press, 1980 pp. 167–179.

J.E. Tomlinson et al., "Rhesus Monkey Apolipoprotein(a)," The Journal of Biological Chemistry, 264:10, Apr. 5, 1989, pp. 5957–5965.

W.C. Taddei–Peters et al., "Quantification of Lipoprotein(a) Particles Containing Various Apolipoprotein(a) Isoforms by a Monoclonal Anti–Apo(a) Capture Antibody and a Polyclonal Anti–Apolipoprotein B Detection Antibody Sandwich Enzyme Immunoassay," Clin. Chem., 39/7, 1382–1389, (1993).

W.J.M. VanGrunsven et al., "Gene Mapping and Expression of Two Immunodominant Epstein–Barr Virus Capsid Proteins" Journal of Virology, vol. 67, pp. 3908–3916, Jul. 1993.

J.W. McLean et al., "cDNA Sequence of Human Apolipoprotein(a) is Homologous to Plasminogen," Nature, vol. 330:12, Nov. 12, 1987, pp. 132–137.

S. Yamada et al., Derwent Abstract of WO/9404563–A1, Mar. 3, 1994.

Primary Examiner—Christina Y. Chan
Assistant Examiner—Mary Beth Tung
Attorney, Agent, or Firm—Mary E. Gormley

[57] ABSTRACT

The present invention relates to peptides immunoreactive with anti-apolipoprotein(a) antibodies and to their use in raising monoclonal and polyclonal antibodies, in immunoassays and of their corresponding oligonucleotides as probes and primers in nucleic acid methodology.

4 Claims, 8 Drawing Sheets

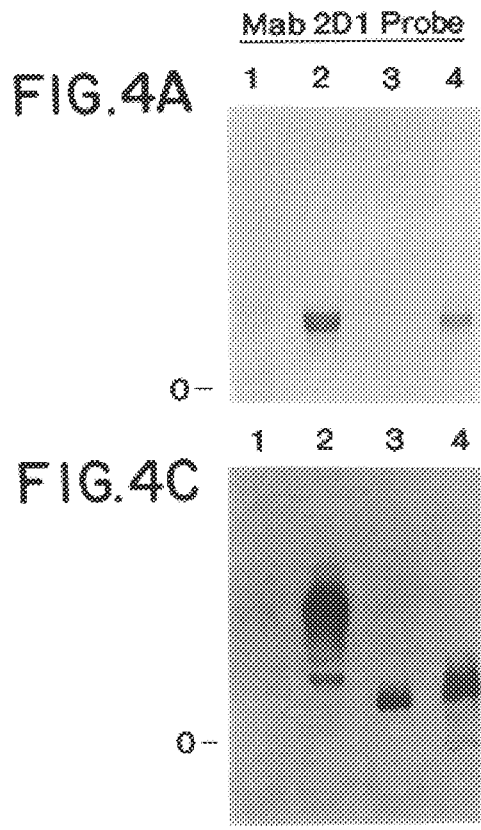
FIG.4A
FIG.4C
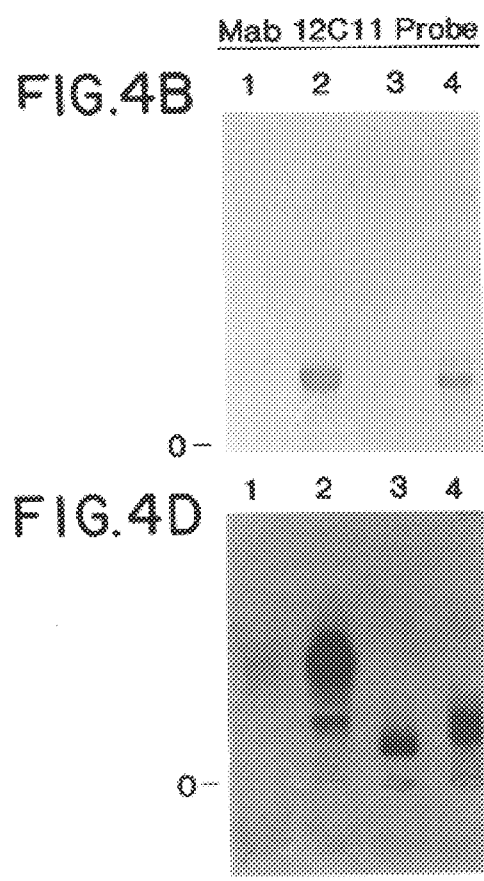
FIG.4B
FIG.4D

```
                        10v       20v       30v       40v       50v
SEQ ID NO: 46)1   IVGGCVAHPHSWPWQVSLRTRFGKHFCGGTLISPEWVLTAAHCLKKSSRPS
SEQ ID NO: 48)2   :VGGCVAHPHSWPWQVSLRTRFG.HFCGGTLISPEWVLTAAHCL.KS:RPS
SEQ ID NO: 47)3   VVGGCVAHPHSWPWQVSLRTRFGMHFCGGTLISPEWVLTAAHCLEKSPRPS
                       590^      600^      610^      620^      630^
                        60v       70v       80v       90v      100v
                1  SYKVILGAHQEVNLESHVQEIEVSRLFLEPTQADIALLKLSRPAVITDKVM
                2  SYKVILGAHQEVNLE:HVQEIEVSRLFLEPT:.DIALLKLS.PAVITDKV:
                3  SYKVILGAHQEVNLEPHVQEIEVSRLFLEPTRKDIALLKLSSPAVITDKVi
                       640^      650^      660^      670^      680^
                       110v      120v      130v      140v      150v
                1  PACLPSPDYMVTARTECYITGWGETQGTFGTGLLKEAQLLVIENEVCNHYK
                2  PACLPSP:Y:V:.RTEC::ITGWGETQGTFG:GLLKEAQL.VIEN..VCN:Y.
                3  PACLPSPNYVVADRTECFITGWGETQGTFGAGLLKEAQLPVIENKVCNRYE
                       690^      700^      710^      720^      730^
                       160v      170v      180v      190v
                1  Y--------ICAEHLARGTDSCQGDSGGPLVCFEKDKYILQGVTSWGLGC
                2  :CA.HLA.GTDSCQGDSGGPLVCFEKDKYILQGVTSWGLGC
                3  FLNGRVQSTELCAGHLAGGTDSCQGDSGGPLVCFEKDKYILQGVTSWGLGC
                       740^      750^      760^      770^      780^
                       200v      210v      220v
                1  ARPNKPGVYARVSRFVTWIEGMMRNNX
                2  ARPNKPGVY.RVSRFVTWIEG:MRNN
                3  ARPNKPGVYVRVSRFVTWIEGVMRNN
                       790^      800^      810^
```

FIG. 8

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 1..33

( x i ) SEQUENCE DESCRIPTION: SEQ ID NO:1:

```
TTC  TTG  GAG  CCC  ACA  CAA  GCA  GAT  ATT  GCC  TTG                    33
Phe  Leu  Glu  Pro  Thr  Gln  Ala  Asp  Ile  Ala  Leu
 1              5                        10
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Phe  Leu  Glu  Pro  Thr  Gln  Ala  Asp  Ile  Ala  Leu
 1              5                        10
```

( 2 ) INFORMATION FOR SEQ ID NO:3:

( i ) SEQUENCE CHARACTERISTICS:

( A ) LENGTH: 39 base pairs
            ( B ) TYPE: nucleic acid
            ( C ) STRANDEDNESS: both
            ( D ) TOPOLOGY: linear ( i i ) MOLECULE TYPE: DNA (genomic)

( i i i ) HYPOTHETICAL: NO ( i x ) FEATURE:
            ( A ) NAME/KEY: CDS
            ( B ) LOCATION: 1..39

( x i ) SEQUENCE DESCRIPTION: SEQ ID NO:3:

```
ACC  GCC  AGG  ACT  GAA  TGT  TAC  ATC  ACT  GGC  TGG  GGA  GAA                    39
Thr  Ala  Arg  Thr  Glu  Cys  Tyr  Ile  Thr  Gly  Trp  Gly  Glu
 1                   5                        10
```

( 2 ) INFORMATION FOR SEQ ID NO:4:

( i ) SEQUENCE CHARACTERISTICS:
            ( A ) LENGTH: 13 amino acids
            ( B ) TYPE: amino acid
            ( D ) TOPOLOGY: linear ( i i ) MOLECULE TYPE: protein ( x i ) SEQUENCE DESCRIPTION: SEQ ID NO:4:

```
Thr  Ala  Arg  Thr  Glu  Cys  Tyr  Ile  Thr  Gly  Trp  Gly  Glu
 1                   5                        10
```

( 2 ) INFORMATION FOR SEQ ID NO:5:

( i ) SEQUENCE CHARACTERISTICS:
            ( A ) LENGTH: 39 base pairs
            ( B ) TYPE: nucleic acid
            ( C ) STRANDEDNESS: both
            ( D ) TOPOLOGY: linear ( i i ) MOLECULE TYPE: DNA (genomic)

( i i i ) HYPOTHETICAL: NO ( i x ) FEATURE:
            ( A ) NAME/KEY: CDS
            ( B ) LOCATION: 1..39

( x i ) SEQUENCE DESCRIPTION: SEQ ID NO:5:

```
CCA  GAC  TAC  ATG  GTC  ACC  GCC  AGG  ACT  GAA  TGT  TAC  ATC                    39
Pro  Asp  Tyr  Met  Val  Thr  Ala  Arg  Thr  Glu  Cys  Tyr  Ile
 1                   5                        10
```

( 2 ) INFORMATION FOR SEQ ID NO:6:

( i ) SEQUENCE CHARACTERISTICS:
            ( A ) LENGTH: 13 amino acids
            ( B ) TYPE: amino acid
            ( D ) TOPOLOGY: linear ( i i ) MOLECULE TYPE: protein ( x i ) SEQUENCE DESCRIPTION: SEQ ID NO:6:

```
Pro  Asp  Tyr  Met  Val  Thr  Ala  Arg  Thr  Glu  Cys  Tyr  Ile
 1                   5                        10
```

( 2 ) INFORMATION FOR SEQ ID NO:7:

( i ) SEQUENCE CHARACTERISTICS:
            ( A ) LENGTH: 39 base pairs
            ( B ) TYPE: nucleic acid
            ( C ) STRANDEDNESS: both
            ( D ) TOPOLOGY: linear (i i) MOLECULE TYPE: DNA (genomic)

(i i i) HYPOTHETICAL: NO (i x) FEATURE:
    (A) NAME/KEY: CDS
    (B) LOCATION: 1..39

(x i) SEQUENCE DESCRIPTION: SEQ ID NO:7:

```
AAG  AAA  TGT  CCT  GGA  AGC  ATT  GTA  GGG  GGG  TGT  GTG  GCC       39
Lys  Lys  Cys  Pro  Gly  Ser  Ile  Val  Gly  Gly  Cys  Val  Ala
 1              5                         10
```

(2) INFORMATION FOR SEQ ID NO:8:

(i) SEQUENCE CHARACTERISTICS:
        (A) LENGTH: 13 amino acids
        (B) TYPE: amino acid
        (D) TOPOLOGY: linear (i i) MOLECULE TYPE: protein (x i) SEQUENCE DESCRIPTION: SEQ ID NO:8:

```
Lys  Lys  Cys  Pro  Gly  Ser  Ile  Val  Gly  Gly  Cys  Val  Ala
 1              5                         10
```

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: both
        (D) TOPOLOGY: linear (i i) MOLECULE TYPE: DNA (genomic)

(i i i) HYPOTHETICAL: NO (i x) FEATURE:
    (A) NAME/KEY: CDS
    (B) LOCATION: 1..39

(x i) SEQUENCE DESCRIPTION: SEQ ID NO:9:

```
CTC  AGA  ACA  AGG  TTT  GGA  AAG  CAC  TTC  TGT  GGA  GGC  ACC       39
Leu  Arg  Thr  Arg  Phe  Gly  Lys  His  Phe  Cys  Gly  Gly  Thr
 1              5                         10
```

(2) INFORMATION FOR SEQ ID NO:10:

(i) SEQUENCE CHARACTERISTICS:
        (A) LENGTH: 13 amino acids
        (B) TYPE: amino acid
        (D) TOPOLOGY: linear (i i) MOLECULE TYPE: protein (x i) SEQUENCE DESCRIPTION: SEQ ID NO:10:

```
Leu  Arg  Thr  Arg  Phe  Gly  Lys  His  Phe  Cys  Gly  Gly  Thr
 1              5                         10
```

(2) INFORMATION FOR SEQ ID NO:11:

(i) SEQUENCE CHARACTERISTICS:
        (A) LENGTH: 39 base pairs
        (B) TYPE: nucleic acid
        (C) STRANDEDNESS: both
        (D) TOPOLOGY: linear (i i) MOLECULE TYPE: DNA (genomic)

(i i i) HYPOTHETICAL: NO ( i x ) FEATURE:
       ( A ) NAME/KEY: CDS
       ( B ) LOCATION: 1..39

( x i ) SEQUENCE DESCRIPTION: SEQ ID NO:11:

```
CAC TGC TTG AAG AAG TCC TCA AGG CCT TCA TCC TAC AAG                    39
His Cys Leu Lys Lys Ser Ser Arg Pro Ser Ser Tyr Lys
 1               5                  10
```

( 2 ) INFORMATION FOR SEQ ID NO:12:

( i ) SEQUENCE CHARACTERISTICS:
       ( A ) LENGTH: 13 amino acids
       ( B ) TYPE: amino acid
       ( D ) TOPOLOGY: linear ( i i ) MOLECULE TYPE: protein ( x i ) SEQUENCE DESCRIPTION: SEQ ID NO:12:

```
His Cys Leu Lys Lys Ser Ser Arg Pro Ser Ser Tyr Lys
 1               5                  10
```

( 2 ) INFORMATION FOR SEQ ID NO:13:

( i ) SEQUENCE CHARACTERISTICS:
       ( A ) LENGTH: 39 base pairs
       ( B ) TYPE: nucleic acid
       ( C ) STRANDEDNESS: both
       ( D ) TOPOLOGY: linear ( i i ) MOLECULE TYPE: DNA (genomic)

( i i i ) HYPOTHETICAL: NO ( i x ) FEATURE:
       ( A ) NAME/KEY: CDS
       ( B ) LOCATION: 1..39

( x i ) SEQUENCE DESCRIPTION: SEQ ID NO:13:

```
CAA GAA GTG AAC CTC GAA TCT CAT GTT CAG GAA ATA GAA                    39
Gln Glu Val Asn Leu Glu Ser His Val Gln Glu Ile Glu
 1               5                  10
```

( 2 ) INFORMATION FOR SEQ ID NO:14:

( i ) SEQUENCE CHARACTERISTICS:
       ( A ) LENGTH: 13 amino acids
       ( B ) TYPE: amino acid
       ( D ) TOPOLOGY: linear ( i i ) MOLECULE TYPE: protein ( x i ) SEQUENCE DESCRIPTION: SEQ ID NO:14:

```
Gln Glu Val Asn Leu Glu Ser His Val Gln Glu Ile Glu
 1               5                  10
```

( 2 ) INFORMATION FOR SEQ ID NO:15:

( i ) SEQUENCE CHARACTERISTICS:
       ( A ) LENGTH: 39 base pairs
       ( B ) TYPE: nucleic acid
       ( C ) STRANDEDNESS: both
       ( D ) TOPOLOGY: linear ( i i ) MOLECULE TYPE: DNA (genomic)

( i i i ) HYPOTHETICAL: NO ( i x ) FEATURE:
       ( A ) NAME/KEY: CDS
       ( B ) LOCATION: 1..39

(x i) SEQUENCE DESCRIPTION: SEQ ID NO:15:

| GCC | TTG | CTA | AAG | CTA | AGC | AGG | CCT | GCC | GTC | ATC | ACT | GAC | 39 |
| Ala | Leu | Leu | Lys | Leu | Ser | Arg | Pro | Ala | Val | Ile | Thr | Asp | |
| 1 | | | | 5 | | | | | 10 | | | | |

(2) INFORMATION FOR SEQ ID NO:16:

(i) SEQUENCE CHARACTERISTICS:
        (A) LENGTH: 13 amino acids
        (B) TYPE: amino acid
        (D) TOPOLOGY: linear (i i) MOLECULE TYPE: protein (x i) SEQUENCE DESCRIPTION: SEQ ID NO:16:

Ala Leu Leu Lys Leu Ser Arg Pro Ala Val Ile Thr Asp
1               5                       10

(2) INFORMATION FOR SEQ ID NO:17:

(i) SEQUENCE CHARACTERISTICS:
        (A) LENGTH: 39 base pairs
        (B) TYPE: nucleic acid
        (C) STRANDEDNESS: both
        (D) TOPOLOGY: linear (i i) MOLECULE TYPE: DNA (genomic)

(i i i) HYPOTHETICAL: NO (i x) FEATURE:
        (A) NAME/KEY: CDS
        (B) LOCATION: 1..39

(x i) SEQUENCE DESCRIPTION: SEQ ID NO:17:

| GAG | AAT | GAA | GTG | TGC | AAT | CAC | TAT | AAG | TAT | ATT | TGT | GCT | 39 |
| Glu | Asn | Glu | Val | Cys | Asn | His | Tyr | Lys | Tyr | Ile | Cys | Ala | |
| 1 | | | | 5 | | | | | 10 | | | | |

(2) INFORMATION FOR SEQ ID NO:18:

(i) SEQUENCE CHARACTERISTICS:
        (A) LENGTH: 13 amino acids
        (B) TYPE: amino acid
        (D) TOPOLOGY: linear (i i) MOLECULE TYPE: protein (x i) SEQUENCE DESCRIPTION: SEQ ID NO:18:

Glu Asn Glu Val Cys Asn His Tyr Lys Tyr Ile Cys Ala
1               5                       10

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: both
        (D) TOPOLOGY: linear (i i) MOLECULE TYPE: DNA (genomic)

(i i i) HYPOTHETICAL: NO (i x) FEATURE:
        (A) NAME/KEY: CDS
        (B) LOCATION: 1..36

(x i) SEQUENCE DESCRIPTION: SEQ ID NO:19:

CTG TTC TTG GAG CCC ACA CAA GCA GAT ATT GCC TTG    36

```
Leu  Phe  Leu  Glu  Pro  Thr  Gln  Ala  Asp  Ile  Ala  Leu
 1              5                        10
```

(2) INFORMATION FOR SEQ ID NO:20:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:20:

```
Leu  Phe  Leu  Glu  Pro  Thr  Gln  Ala  Asp  Ile  Ala  Leu
 1              5                        10
```

(2) INFORMATION FOR SEQ ID NO:21:

(i) SEQUENCE CHARACTERISTICS:
        (A) LENGTH: 36 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: 1..36

(xi) SEQUENCE DESCRIPTION: SEQ ID NO:21:

```
TTC  TTG  GAG  CCC  ACA  CAA  GCA  GAT  ATT  GCC  TTG  CTA    36
Phe  Leu  Glu  Pro  Thr  Gln  Ala  Asp  Ile  Ala  Leu  Leu
 1              5                        10
```

(2) INFORMATION FOR SEQ ID NO:22:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:22:

```
Phe  Leu  Glu  Pro  Thr  Gln  Ala  Asp  Ile  Ala  Leu  Leu
 1              5                        10
```

(2) INFORMATION FOR SEQ ID NO:23:

(i) SEQUENCE CHARACTERISTICS:
        (A) LENGTH: 15 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: 1..15

(xi) SEQUENCE DESCRIPTION: SEQ ID NO:23:

```
CCC  ACA  CAA  GCA  GAT    15
Pro  Thr  Gln  Ala  Asp
 1              5
```

( 2 ) INFORMATION FOR SEQ ID NO:24:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

Pro Thr Gln Ala Asp
 1               5

( 2 ) INFORMATION FOR SEQ ID NO:25:

( i ) SEQUENCE CHARACTERISTICS:
        ( A ) LENGTH: 15 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..15

( x i ) SEQUENCE DESCRIPTION: SEQ ID NO:25:

GAA TGT TAC ATC ACT                                      15
Glu Cys Tyr Ile Thr
 1               5

( 2 ) INFORMATION FOR SEQ ID NO:26:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

Glu Cys Tyr Ile Thr
 1               5

( 2 ) INFORMATION FOR SEQ ID NO:27:

( i ) SEQUENCE CHARACTERISTICS:
        ( A ) LENGTH: 15 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..15

( x i ) SEQUENCE DESCRIPTION: SEQ ID NO:27:

GTC ACC GCC AGG ACT                                      15
Val Thr Ala Arg Thr
 1               5

( 2 ) INFORMATION FOR SEQ ID NO:28:

( i ) SEQUENCE CHARACTERISTICS:
        ( A ) LENGTH: 5 amino acids (B) TYPE: amino acid
(D) TOPOLOGY: linear (i i) MOLECULE TYPE: protein (x i) SEQUENCE DESCRIPTION: SEQ ID NO:28:

Val Thr Ala Arg Thr
1               5

(2) INFORMATION FOR SEQ ID NO:29:

(i) SEQUENCE CHARACTERISTICS:
(A) LENGTH: 15 base pairs
(B) TYPE: nucleic acid
(C) STRANDEDNESS: both
(D) TOPOLOGY: linear (i i) MOLECULE TYPE: DNA (genomic)

(i i i) HYPOTHETICAL: NO (i x) FEATURE:
(A) NAME/KEY: CDS
(B) LOCATION: 1..15

(x i) SEQUENCE DESCRIPTION: SEQ ID NO:29:

GGA AGC ATT GTA GGG                                                        15
Gly Ser Ile Val Gly
1               5

(2) INFORMATION FOR SEQ ID NO:30:

(i) SEQUENCE CHARACTERISTICS:
(A) LENGTH: 5 amino acids
(B) TYPE: amino acid
(D) TOPOLOGY: linear (i i) MOLECULE TYPE: protein (x i) SEQUENCE DESCRIPTION: SEQ ID NO:30:

Gly Ser Ile Val Gly
1               5

(2) INFORMATION FOR SEQ ID NO:31:

(i) SEQUENCE CHARACTERISTICS:
(A) LENGTH: 15 base pairs
(B) TYPE: nucleic acid
(C) STRANDEDNESS: both
(D) TOPOLOGY: linear (i i) MOLECULE TYPE: DNA (genomic)

(i i i) HYPOTHETICAL: NO (i x) FEATURE:
(A) NAME/KEY: CDS
(B) LOCATION: 1..15

(x i) SEQUENCE DESCRIPTION: SEQ ID NO:31:

TTT GGA AAG CAC TTC                                                        15
Phe Gly Lys His Phe
1               5

(2) INFORMATION FOR SEQ ID NO:32:

(i) SEQUENCE CHARACTERISTICS:
(A) LENGTH: 5 amino acids
(B) TYPE: amino acid
(D) TOPOLOGY: linear (i i) MOLECULE TYPE: protein ( x i ) SEQUENCE DESCRIPTION: SEQ ID NO:32:

Phe  Gly  Lys  His  Phe
 1                    5

( 2 ) INFORMATION FOR SEQ ID NO:33:

( i ) SEQUENCE CHARACTERISTICS:
        ( A ) LENGTH: 15 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..15

( x i ) SEQUENCE DESCRIPTION: SEQ ID NO:33:

AAG  TCC  TCA  AGG  CCT                                                                 15
Lys  Ser  Ser  Arg  Pro
 1                    5

( 2 ) INFORMATION FOR SEQ ID NO:34:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:34:

Lys  Ser  Ser  Arg  Pro
 1                    5

( 2 ) INFORMATION FOR SEQ ID NO:35:

( i ) SEQUENCE CHARACTERISTICS:
        ( A ) LENGTH: 15 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..15

( x i ) SEQUENCE DESCRIPTION: SEQ ID NO:35:

CTC  GAA  TCT  CAT  GTT                                                                 15
Leu  Glu  Ser  His  Val
 1                    5

( 2 ) INFORMATION FOR SEQ ID NO:36:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

Leu  Glu  Ser  His  Val ( 2 ) INFORMATION FOR SEQ ID NO:37:

( i ) SEQUENCE CHARACTERISTICS:
        ( A ) LENGTH: 15 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..15

( x i ) SEQUENCE DESCRIPTION: SEQ ID NO:37:

```
CTA  AGC  AGG  CCT  GCC                                              15
Leu  Ser  Arg  Pro  Ala
 1                 5
```

( 2 ) INFORMATION FOR SEQ ID NO:38:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

```
Leu  Ser  Arg  Pro  Ala
 1                 5
```

( 2 ) INFORMATION FOR SEQ ID NO:39:

( i ) SEQUENCE CHARACTERISTICS:
        ( A ) LENGTH: 15 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..15

( x i ) SEQUENCE DESCRIPTION: SEQ ID NO:39:

```
TGC  AAT  CAC  TAT  AAG                                              15
Cys  Asn  His  Tyr  Lys
 1                 5
```

( 2 ) INFORMATION FOR SEQ ID NO:40:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

```
Cys  Asn  His  Tyr  Lys
 1                 5
```

( 2 ) INFORMATION FOR SEQ ID NO:41:

-continued ( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i i ) HYPOTHETICAL: NO ( x i ) SEQUENCE DESCRIPTION: SEQ ID NO:41:

AGCTAGGAAT CCGAATCGAG TGTCCTCACA ACT   33

( 2 ) INFORMATION FOR SEQ ID NO:42:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i i ) HYPOTHETICAL: NO ( x i ) SEQUENCE DESCRIPTION: SEQ ID NO:42:

AGCTAGGGAT CCATTCATTG TGTAGCACCA GGGACC   36

( 2 ) INFORMATION FOR SEQ ID NO:43:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i i ) HYPOTHETICAL: NO ( x i ) SEQUENCE DESCRIPTION: SEQ ID NO:43:

AGCTAGGGAT CCGTAGGTTG ATGCTTCACT CTG   33

( 2 ) INFORMATION FOR SEQ ID NO:44:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i i ) HYPOTHETICAL: NO ( x i ) SEQUENCE DESCRIPTION: SEQ ID NO:44:

AGCTAGGGAT CCCAAGACTG TATGTTTGGG AAT   33

( 2 ) INFORMATION FOR SEQ ID NO:45:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i i ) HYPOTHETICAL: NO ( x i ) SEQUENCE DESCRIPTION: SEQ ID NO:45:

AGCTAGGGAT CCATTGTAGG GGGGTGTGTG GCC   33

( 2 ) INFORMATION FOR SEQ ID NO:46:

( i ) SEQUENCE CHARACTERISTICS:
    ( A ) LENGTH: 222 amino acids
    ( B ) TYPE: amino acid
    ( C ) STRANDEDNESS: single (D) TOPOLOGY: linear (ii) MOLECULE TYPE: peptide (iii) HYPOTHETICAL: NO (v) FRAGMENT TYPE: C-terminal (vi) ORIGINAL SOURCE:
    (A) ORGANISM: Homo sapiens (xi) SEQUENCE DESCRIPTION: SEQ ID NO:46:

| Ile | Val | Gly | Gly | Cys | Val | Ala | His | Pro | His | Ser | Trp | Pro | Trp | Gln | Val |
|---|---|---|---|---|---|---|---|---|---|---|---|---|---|---|---|
| 1 | | | | 5 | | | | | 10 | | | | | 15 | |

| Ser | Leu | Arg | Thr | Arg | Phe | Gly | Lys | His | Phe | Cys | Gly | Gly | Thr | Leu | Ile |
|---|---|---|---|---|---|---|---|---|---|---|---|---|---|---|---|
| | | | 20 | | | | 25 | | | | | | 30 | | |

| Ser | Pro | Glu | Trp | Val | Leu | Thr | Ala | Ala | His | Cys | Leu | Lys | Lys | Ser | Ser |
|---|---|---|---|---|---|---|---|---|---|---|---|---|---|---|---|
| | | 35 | | | | | 40 | | | | | 45 | | | |

| Arg | Pro | Ser | Ser | Tyr | Lys | Val | Ile | Leu | Gly | Ala | His | Gln | Glu | Val | Asn |
|---|---|---|---|---|---|---|---|---|---|---|---|---|---|---|---|
| | 50 | | | | | 55 | | | | | 60 | | | | |

| Leu | Glu | Ser | His | Val | Gln | Glu | Ile | Glu | Val | Ser | Arg | Leu | Phe | Leu | Glu |
|---|---|---|---|---|---|---|---|---|---|---|---|---|---|---|---|
| 65 | | | | | 70 | | | | | 75 | | | | | 80 |

| Pro | Thr | Gln | Ala | Asp | Ile | Ala | Leu | Leu | Lys | Leu | Ser | Arg | Pro | Ala | Val |
|---|---|---|---|---|---|---|---|---|---|---|---|---|---|---|---|
| | | | | 85 | | | | | 90 | | | | | 95 | |

| Ile | Thr | Asp | Lys | Val | Met | Pro | Ala | Cys | Leu | Pro | Ser | Pro | Asp | Tyr | Met |
|---|---|---|---|---|---|---|---|---|---|---|---|---|---|---|---|
| | | | 100 | | | | | 105 | | | | | 110 | | |

| Val | Thr | Ala | Arg | Thr | Glu | Cys | Tyr | Ile | Thr | Gly | Trp | Gly | Glu | Thr | Gln |
|---|---|---|---|---|---|---|---|---|---|---|---|---|---|---|---|
| | | 115 | | | | | 120 | | | | | 125 | | | |

| Gly | Thr | Phe | Gly | Thr | Gly | Leu | Leu | Lys | Glu | Ala | Gln | Leu | Leu | Val | Ile |
|---|---|---|---|---|---|---|---|---|---|---|---|---|---|---|---|
| | 130 | | | | | 135 | | | | | 140 | | | | |

| Glu | Asn | Glu | Val | Cys | Asn | His | Tyr | Lys | Tyr | Ile | Cys | Ala | Glu | His | Leu |
|---|---|---|---|---|---|---|---|---|---|---|---|---|---|---|---|
| 145 | | | | | 150 | | | | | 155 | | | | | 160 |

| Ala | Arg | Gly | Thr | Asp | Ser | Cys | Gln | Gly | Asp | Ser | Gly | Gly | Pro | Leu | Val |
|---|---|---|---|---|---|---|---|---|---|---|---|---|---|---|---|
| | | | | 165 | | | | | 170 | | | | | 175 | |

| Cys | Phe | Glu | Lys | Asp | Lys | Tyr | Ile | Leu | Gln | Gly | Val | Thr | Ser | Trp | Gly |
|---|---|---|---|---|---|---|---|---|---|---|---|---|---|---|---|
| | | | 180 | | | | | 185 | | | | | 190 | | |

| Leu | Gly | Cys | Ala | Arg | Pro | Asn | Lys | Pro | Gly | Val | Tyr | Ala | Arg | Val | Ser |
|---|---|---|---|---|---|---|---|---|---|---|---|---|---|---|---|
| | | 195 | | | | | 200 | | | | | 205 | | | |

| Arg | Phe | Val | Thr | Trp | Ile | Glu | Gly | Met | Met | Arg | Asn | Asn | Xaa | | |
|---|---|---|---|---|---|---|---|---|---|---|---|---|---|---|---|
| | 210 | | | | | 215 | | | | | 220 | | | | |

(2) INFORMATION FOR SEQ ID NO:47:

(i) SEQUENCE CHARACTERISTICS:
    (A) LENGTH: 230 amino acids
    (B) TYPE: amino acid
    (C) STRANDEDNESS: single
    (D) TOPOLOGY: linear (ii) MOLECULE TYPE: peptide (iii) HYPOTHETICAL: NO (v) FRAGMENT TYPE: C-terminal (vi) ORIGINAL SOURCE:
    (A) ORGANISM: Homo sapiens (xi) SEQUENCE DESCRIPTION: SEQ ID NO:47:

| Val | Val | Gly | Gly | Cys | Val | Ala | His | Pro | His | Ser | Trp | Pro | Trp | Gln | Val |
|---|---|---|---|---|---|---|---|---|---|---|---|---|---|---|---|
| 1 | | | | 5 | | | | | 10 | | | | | 15 | |

| Ser | Leu | Arg | Thr | Arg | Phe | Gly | Met | His | Phe | Cys | Gly | Gly | Thr | Leu | Ile |
|---|---|---|---|---|---|---|---|---|---|---|---|---|---|---|---|
| | | | 20 | | | | 25 | | | | | | 30 | | |

|   |   |   |   |   |   |   |   |   |   |   |   |   |   |   |
|---|---|---|---|---|---|---|---|---|---|---|---|---|---|---|
| Ser | Pro | Glu<br>35 | Trp | Val | Leu | Thr | Ala<br>40 | Ala | His | Cys | Leu | Glu<br>45 | Lys | Ser | Pro |
| Arg | Pro<br>50 | Ser | Ser | Tyr | Lys<br>55 | Val | Ile | Leu | Gly | Ala<br>60 | His | Gln | Glu | Val | Asn |
| Leu<br>65 | Glu | Pro | His | Val | Gln<br>70 | Glu | Ile | Glu | Val | Ser<br>75 | Arg | Leu | Phe | Leu | Glu<br>80 |
| Pro | Thr | Arg | Lys | Asp<br>85 | Ile | Ala | Leu | Leu | Lys<br>90 | Leu | Ser | Ser | Pro | Ala<br>95 | Val |
| Ile | Thr | Asp | Lys<br>100 | Val | Ile | Pro | Ala | Cys<br>105 | Leu | Pro | Ser | Pro | Asn<br>110 | Tyr | Val |
| Val | Ala | Asp<br>115 | Arg | Thr | Glu | Cys | Phe<br>120 | Ile | Thr | Gly | Trp | Gly<br>125 | Glu | Thr | Gln |
| Gly | Thr<br>130 | Phe | Gly | Ala | Gly | Leu<br>135 | Leu | Lys | Glu | Ala | Gln<br>140 | Leu | Pro | Val | Ile |
| Glu<br>145 | Asn | Lys | Val | Cys | Asn<br>150 | Arg | Tyr | Glu | Phe | Leu<br>155 | Asn | Gly | Arg | Val | Gln<br>160 |
| Ser | Thr | Glu | Leu | Cys<br>165 | Ala | Gly | His | Leu | Ala<br>170 | Gly | Gly | Thr | Asp | Ser<br>175 | Cys |
| Gln | Gly | Asp | Ser<br>180 | Gly | Gly | Pro | Leu | Val<br>185 | Cys | Phe | Glu | Lys | Asp<br>190 | Lys | Tyr |
| Ile | Leu | Gln | Gly<br>195 | Val | Thr | Ser | Trp | Gly<br>200 | Leu | Gly | Cys | Ala | Arg<br>205 | Pro | Asn |
| Lys | Pro<br>210 | Gly | Val | Tyr | Val | Arg<br>215 | Val | Ser | Arg | Phe | Val<br>220 | Thr | Trp | Ile | Glu |
| Gly<br>225 | Val | Met | Arg | Asn | Asn<br>230 |   |   |   |   |   |   |   |   |   |   |

( 2 ) INFORMATION FOR SEQ ID NO:48:

( i ) SEQUENCE CHARACTERISTICS:
        ( A ) LENGTH: 197 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:48:

|   |   |   |   |   |   |   |   |   |   |   |   |   |   |   |
|---|---|---|---|---|---|---|---|---|---|---|---|---|---|---|
| Val<br>1 | Gly | Gly | Cys | Val<br>5 | Ala | His | Pro | His | Ser<br>10 | Trp | Pro | Trp | Gln | Val<br>15 | Ser |
| Leu | Arg | Thr | Arg<br>20 | Phe | Gly | His | Phe | Cys<br>25 | Gly | Gly | Thr | Leu | Ile<br>30 | Ser | Pro |
| Glu | Trp | Val | Leu | Thr<br>35 | Ala | Ala | His | Cys<br>40 | Leu | Lys | Ser | Arg<br>45 | Pro | Ser | Ser |
| Tyr | Lys<br>50 | Val | Ile | Leu | Gly | Ala<br>55 | His | Gln | Glu | Val | Asn<br>60 | Leu | Glu | His | Val |
| Gln<br>65 | Glu | Ile | Glu | Val | Ser<br>70 | Arg | Leu | Phe | Leu | Glu<br>75 | Pro | Thr | Asp | Ile | Ala<br>80 |
| Ser | Leu | Leu | Lys | Leu<br>85 | Ser | Pro | Ala | Val | Ile<br>90 | Thr | Asp | Lys | Val | Pro<br>95 | Ala |
| Cys | Leu | Pro | Ser<br>100 | Pro | Tyr | Val | Arg | Thr<br>105 | Glu | Cys | Ile | Thr | Gly<br>110 | Trp | Gly |
| Glu | Thr | Gln<br>115 | Gly | Thr | Phe | Gly | Gly<br>120 | Leu | Leu | Lys | Glu | Ala<br>125 | Gln | Leu | Val |
| Ile | Glu | Asn | Val | Cys | Asn | Tyr | Cys | Ala | His | Leu | Ala | Gly | Thr | Asp | Ser |

-continued

|   |   |   | 130 |   |   |   | 135 |   |   |   | 140 |   |   |   |
|---|---|---|---|---|---|---|---|---|---|---|---|---|---|---|
| Cys 145 | Gln | Gly | Asp | Ser | Gly 150 | Gly | Pro | Leu | Val | Cys 155 | Phe | Glu | Lys | Asp | Lys 160 |
| Tyr | Ile | Leu | Gln | Gly 165 | Val | Thr | Ser | Trp | Gly 170 | Leu | Gly | Cys | Ala | Arg 175 | Pro |
| Asn | Lys | Pro | Gly 180 | Val | Tyr | Arg | Val | Ser 185 | Arg | Phe | Val | Thr | Trp 190 | Ile | Glu |
| Gly | Met | Arg 195 | Asn | Asn |

ANTIBODIES TO APO(A)

This is a divisional of application U.S. Ser. No. 08/457,449, filed Jun. 1, 1995, now U.S. Pat. No. 5,708,138, which is a divisional of U.S. Ser. No. 08/266,407, filed Jun. 27, 1994, now U.S. Pat. No. 5,786,156, which is a continuation-in-part of U.S. Ser. No 08/172,461, filed Dec. 21, 1993, now abandoned.

FIELD OF THE INVENTION

The present invention relates to peptides immunoreactive with anti-apolipoprotein(a) antibodies and to their use in raising monoclonal and polyclonal antibodies and their use in immunoassays, and to their corresponding oligonucleotides which are useful as probes and primers in nucleic acid methodologies.

BACKGROUND OF THE INVENTION

The lipoproteins, which include chylomicrons, very-low-density lipoproteins (VLDL), low-density-lipoproteins (LDL), and high-density-lipoproteins (HDL), are the primary carriers of plasma cholesterol. These particles are composed of various proportions of triglycerides, cholesterol, cholesterol ester, phospholipids and proteins. The latter are known as apolipoproteins and play a key role in the metabolism of lipoproteins. Some activate enzymes that are important in the covalent modification of lipids and in the remodeling of lipoprotein subfractions while others serve as receptor ligands that target remodeled lipoproteins to specific tissue sites where their respective lipid components are stored or used.

Lipoprotein(a) is a class of lipoprotein particles similar to LDL, but distinct due to the covalent linkage of apo B100 to apolipoprotein(a) ("apo(a)"), a glycoprotein with significant homology to plasminogen. High plasma concentrations of Lp(a) are associated with an increased risk of atherosclerotic disorders including intermittent claudication, aortic aneurysms, coronary artery stenosis, myocardial infarction and cerebral infarction. Studies implicating the role of Lp(a) in atherogenesis have focused on the binding of Lp(a) to endothelial cells and macrophages and to extracellular plasma proteins such as fibrin. In vitro studies with human fibroblasts and monocytes have demonstrated that Lp(a) is taken up by the LDL receptor. In addition, lipid peroxidation of Lp(a) results in uptake by the scavenger receptor on macrophages. The scavenger receptor is structurally different than the LDL receptor and is thought to play a role in lipid peroxide modified LDL uptake in atheromas. It has been demonstrated by immunohistochemistry that apo(a) and apo B are present in arterial wall plaques. Lp(a)-like particles can be isolated from plaques. Furthermore, a correlation between serum Lp(a) levels and amounts of apo(a) in arterial walls has been reported.

Some studies have implicated a role for Lp(a) in athero-thrombosis due to the homology between apo(a) and plasminogen. Lp(a) competes with plasminogen for binding to fibrin. Because Lp(a) does not enzymatically cleave fibrin, it could inhibit fibrin clot dissolution. Thrombus formation in the intra-coronary arteries is thought to be the major cause of myocardial infarction. Thus, Lp(a) may have a multimodal mechanism in atherogenesis.

Apo(a) is highly heterogeneous in size with reports of 19 to 34 different alleles (Lackner, C. et al., J. Clin. Invest., 87:2158–61 (1991); Kamboh, M. et al., Am. J. Hum. Genet., 49:1063–74 (1991); Marcovina, S. et al., Biochem. Biophys. Res. Comm., 191:1192–6 (1993)). Utermann and co-workers (J. Clin. Invest. 80:458–67 (1987) and Sandholzer et al., Arterio and Thromb. 12:1214–26 (1992)) have designated six different isoform categories, and Marcovina et al. (Arterio and Thromb. 13:1037–45 (1993)) have added a seventh according to electrophoretic mobility compared with that of apo B. The assigned approximate molecular weights to each category are listed in Table 1 below. Apo(a) polymorphism is due to a series of alleles each coding for isoforms differing in the number of Kringle 4 domains (structurally similar to Kringle 4 in plasminogen). Apo(a) contains 5 to 37 Kringle 4 repeats, one Kringle 5 domain and an inactive serine protease region which has 94% homology to plasminogen, as seen in FIG. 1. Thus, size differences in the apo(a) phenotypes are due primarily to the number of Kringle 4 repeat units in apo(a), although differences in glycosylation may also contribute.

TABLE 1

Approximate Molecular Weights of Apo(a) Isoform Categories per Utermann et al.

| Isoform Category | Approximate apo(a) MW |
| --- | --- |
| F | 400,000 |
| B | 460,000 |
| S1 | 520,000 |
| S2 | 580,000 |
| S3 | 640,000 |
| S4 | 700,000 |
| S5 | 760,000 |

Genetic size polymorphisms are associated with plasma Lp(a) concentrations. Low molecular weight isoform categories (F, B, S1 and S2) are associated with high Lp(a) concentrations and high -molecular weight isoform categories (S3, S4 and S5) are associated with low plasma Lp(a) concentrations (Gaubatz, J. et al., J. Lipid Res. 31:603–13 (1990)). Thus, Lp(a) concentrations are thought to be genetically regulated. Furthermore, because elevates Lp(a) levels are associated with increased risk of atherosclerotic diseases, an association has been reported between apo(a) isoform category and risk of coronary artery disease.

Several methods have been developed over the past several decades to measure Lp(a). Initially, Lp(a) was identified by electrophoresis in starch or agar gels under non-denaturing conditions and lipid-binding stains were used for visualization. However, this method was qualitative, not quantitative. Radial immunodiffusion (RID), electroimmunodiffusion (EID), and immunoelectrophoresis (IEP) methods were developed when purified antibodies became available. RID lacked the sensitivity required to measure Lp(a) in all serum and plasma samples and, more importantly, was influenced by the differences in the Lp(a) particle size. However, both EID and IEP, used in the majority of studies associating increased Lp(a) with risk of cardiovascular disease, are accurate and sensitive. Nevertheless, these methods are laborious, time-consuming, and not well suited for studies involving a large number of samples. In addition, neither method lends itself to automation. Immunoturbidimetric and immunonephelometric methods are affected by high concentrations of triglycerides and by freezing the sample. Additionally, the nephelometric method is also highly sensitive to differences in the size of the Lp(a) particle being measured because of the accompanying differences in light-scattering properties. Radioimmunoassays (RIAs) are both sensitive and specific; however, the radioactive component has a limited shelf-life and requires dedicated equipment as well as special handling.

To overcome the problems associated with these methods, the immunoassay known as the sandwich ELISA was developed. However, the ELISA method must be applied with an understanding of the unique molecular characteristics of the Lp(a) particle, which is heterogeneous in size and density. One type of commercially available Lp(a) ELISA assay makes use of a mouse monoclonal anti-apo(a) antibody as the capture antibody and a sheep polyclonal anti-apo B-peroxidase conjugate as the detection system.

Any immunoassay method used to quantify Lp(a) should employ an antibody that recognizes all isoforms equally well; thus, only an antibody that recognizes a non-repetitive epitope within the apo(a) molecule and that does not occur within the plasminogen molecule should be employed in the assay. Since the Kringle 4 domains of apo(a) are highly repetitive, the epitope should exist within either the Kringle 5 or protease-like domains. However, according to J. E. Tomlinson et al. (J. Biol. Chem. 264:5957–65,1989)), rhesus monkey apo(a) does not contain a Kringle 5 domain; therefore, in order to develop an assay for the quantitation of Lp(a) in this common animal model and, possibly, other Old World monkey species (baboons, African green and cynomologous monkeys), the antibody employed must recognize a unique, non-repetitive epitope within only the protease domain of apo(a), i.e., one that does not occur in the plasminogen molecule. Because the protease domain of human apo(a) has a 94% homology to human plasminogen, the likelihood of obtaining an antibody which recognizes a non-repetitive epitope unique to only apo(a) is quite small.

Such an antibody has been developed and is in use in the commercially available ELISA Lp(a) assay mentioned above. However, it would be desirable to know the exact amino acid sequence of the reactive epitopes so that assays using such epitopes or peptides to detect Lp(a) can be developed. The DNA nucleotides that code for these peptides, when reproduced, could be used in nucleic acid based detection and amplification technologies to detect or quantitate apo(a). Also, antibodies against apo(a), both monoclonal and polyclonal, could be raised when such a peptide is used as an antigen in a suitable animal.

BRIEF DESCRIPTION OF THE INVENTION

According to the present invention, a peptide comprising the amino acid sequence

FLEPTQADIAL (SEQ ID NO:2)

has been found to bind to and immunologically detect antibodies to apo(a). For example, one variety of anti-apo(a) monoclonal antibody developed is characterized as not only immunoreactive with the SEQ ID NO:1 peptide but also with apo(a) in Lp(a), isolated apo(a), and apo(a) protease domain. This antibody does not immunoreact with Kringle 5 domain and a large sequence of the Kringle 4 domains, i.e., part of the 35th and all of the 36th and 37th Kringle 4 domains which are highly repetitive.

Other non-repetitive peptides that would be immunologically reactive with anti-apo(a) antibodies as above are:

TARTECYITGWGE (SEQ ID NO:4)
PDYMVTARTECYI (SEQ ID NO:6)
KKCPGSIVGGCVA (SEQ ID NO:8)
LRTRFGKHFCGGT (SEQ ID NO:10)
HCLKKSSRPSSYK (SEQ ID NO:12)
QEVNLESHVQEIE (SEQ ID NO:14)
ALLKLSRPAVITD (SEQ ID NO:16)
ENEVCNHYKYICA (SEQ ID NO:18)

The peptides of SEQ ID NOS:2, 4, 6, 8, 10, 12, 14, 16 and 18, and immunologically functional fragments, larger peptides comprising these sequences and analogues of these peptides, are useful in immunoassays that bind to antibodies in order to compete with apo(a) in serum or plasma for quantitation of apo(a) or Lp(a) in these test specimens, such as a competitive inhibition ELISA immunoassay. They are also useful in raising polyclonal and monoclonal antibodies against apo(a) for use in immunoassays that detect and quantify levels of Lp(a) or apo(a) in test sera or plasma. The DNA nucleotides coding for these peptides can be used as probes or primers in nucleic acid based methodologies, such as NASBA™ (Nucleic Acid Sequence Based Amplification, as described in Kievits et al., J. Virol. Methods, 35:273–286, hereby incorporated by reference), the polymerase chain reaction, or any other sequence based amplification technology.

With respect to using the unique peptides to immunize an animal to raise antibodies or develop monoclonals, only portions of the above-noted peptides containing as little as five amino acids need to be used. These smaller peptides are only limited with respect to whether they can elicit antibodies against apo(a) that do not react with plasminogen; thus, they need to contain the amino acid sequence that is unique to apo(a). For example, the following peptides satisfy this requirement, whereby the amino acid that is unique to apo(a) as compared to plasminogen is located in the middle of the sequence, but by no means is the present invention limited to these examples:

PTQAD (SEQ ID NO:24)
ECYIT (SEQ ID NO:26)
VTART (SEQ ID NO:28)
GSIVG (SEQ ID NO:30)
FGKHF (SEQ ID NO:32)
KSSRP (SEQ ID NO:34)
LESHV (SEQ ID NO:36)
LSRPA (SEQ ID NO:38)
CNHYK (SEQ ID NO:40)

Other peptides where the unique amino acid is other than in the middle are also contemplated as useful in the present invention.

The term "peptide" is defined as a compound formed of two or more amino acids joined by peptide bonds and is not intended to imply any particular size limitation on the molecule. In addition, if required the peptide can be modified in vivo or in vitro, for example by glycosylation, amidation, carboxylation or phosphorylation.

BRIEF DESCRIPTION OF THE DRAWINGS

FIGS. 4A–D show the electrophoresis and Western blot analysis of isolated lipoproteins probed with monoclonal antibodies against apo(a).

In FIG. 5A, the antibody probe is 4F3, which recognizes a repetitive epitope. The antibody probe in FIG. 5B is 2D1, and the antibody probe in FIG. 5C is 12C11, which recognizes a repetitive epitope.

In FIG. 6, ○=2D1; Δ=12C11; ◊=anti-apo B Mab 2B4; and □=anti-apo A Mab 4A2.

FIG. 8 compares the amino acid sequences of the human apo(a) protease domain and human plasminogen. The amino acid sequence of human apo(a) protease domain is shown on line 1 (top), and the sequence of human plasminogen is shown on line 3 (bottom). Line 2 (middle) indicates identical amino acid residues between the apo(a) and plasminogen molecules.

DETAILED DESCRIPTION OF THE INVENTION

Figure 1:
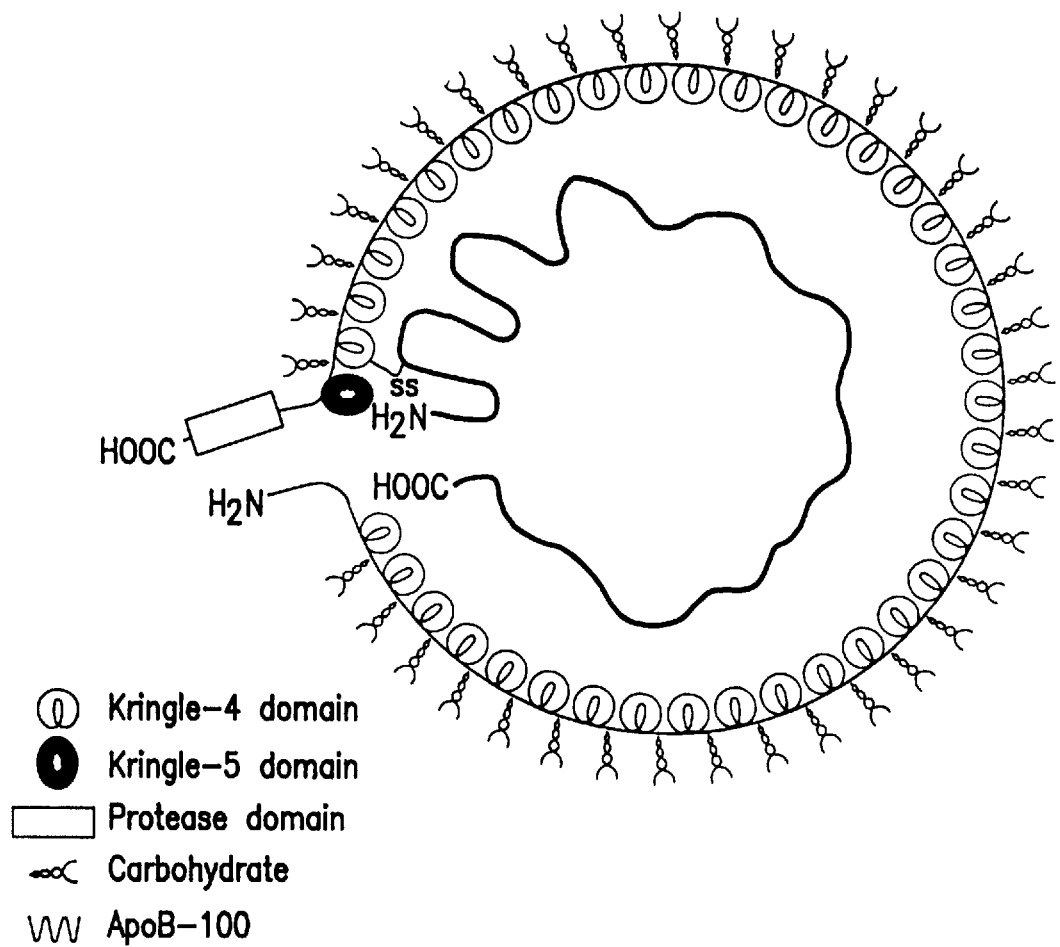
FIG. 1 is a schematic representation of Lp(a) and apo B.

One commercial ELISA assay developed to detect and quantitate levels of Lp(a) in human plasma is performed as follows. Microtiter wells coated with an anti-apo(a) mouse monoclonal antibody ("Mab") are contacted with plasma, incubated and washed. Then, horseradish peroxide ("HRP") -labeled sheep anti-human apo B is added to the wells, incubated and washed. The color is developed by the addition of tetramethylbenzidene ("TMB") substrate and the wells are read for absorbance. Levels, if any, of Lp(a) are determined.

A monoclonal antibody used in this assay, 2D1, is characterized as being immunoreactive with apo(a) in Lp(a), isolated apo(a), apo(a) protease domain, but not with the Kringle 5 domain, a large sequence of the Kringle 4 domains, i.e., part of the 35th and all of the 36th and 37th Kringle 4 domains that are highly repetitive.

In order to more fully characterize 2D1, an epitope on apo(a) with which 2D1 immunoreacts were discovered. The peptide with the following amino acid residue sequence was discovered to be highly reactive with 2D1:

FLEPTQADIAL (SEQ ID NO:2).

This peptide can be obtained from the apo(a) molecule itself or produced either through recombinant means and isolated and purified or chemically synthesized. This peptide is useful for the detection of apo(a) in the body fluids (such as plasma and serum) of mammals by way of, for instance, a competitive inhibition ELISA, and for the development of monoclonal and polyclonal antibodies to apo(a) that can be used inter alia in immunoassays for the detection of apo(a) in body fluids such as serum or plasma.

The peptide of SEQ ID NO:2 was elucidated as containing the reactive epitope for 2D1 by way of the PEPSCAN method described in van Grunsven, W. M. J., *J. Virol.* 67: 3908–3916 (1993), and in U.S. Pat. No. 4,833,092 and WO 84/03564, all incorporated herein by reference. By this method, two overlapping 12-mer peptides reacted strongly with monoclonal antibody 2D1. These peptides are:

LFLEPTQADIAL (SEQ ID NO:20); and
FLEPTQADIALL (SEQ ID NO:22).

It became clear from these results that the epitope for 2D1 is contained in the overlapping portion; i.e., the peptide of SEQ ID NO:2. This peptide contains an amino acid residue (alanine) which is different from the amino acid residue at the corresponding position on plasminogen. This would explain why 2D1 reacts with apo(a) and not with plasminogen.

Once the amino acid sequence of the protease region of the apo(a) molecule was determined and aligned with the corresponding region of plasminogen, the present inventors discovered several peptide fragments that would be useful in raising antibodies that could be used in immunoassays for the quantitative determination of apo(a). Specifically, as with the peptide of SEQ ID NO:2, these peptide fragments each contain an amino acid residue that is different from the amino acid residue on the corresponding plasminogen molecule. These peptide fragments, which may contain as little as five amino acid residues provided they contain the amino acid that is different from the corresponding plasminogen amino acid, can be used to immunize animals in order to raise polyclonal antibodies or to prepare monoclonal antibodies by methods known in the art. Such small fragments are usually conjugated to larger carrier proteins in order to elicitian immunological response. Methods of conjugating peptides to larger protein molecules are known in the art (see, for instance, *Antibodies: A laboratory manual,* Harlow and Lane, Cold Spring Harbor Laboratory Press, 1988, incorporated herein by reference). The peptides that would be particularly useful in raising antibodies specific for apo(a) are all of the peptides comprising the sequences of SEQ ID NOS: 2, 4, 6, 8, 10, 12, 14. 16, 18, 20, 22, 24, 26, 28, 30, 32, 34, 36, 38 and 40.

In addition to the possibility that each of the peptides of the present invention may be shorter than the sequences given herein (provided each fragment contains at least five amino acids with the unique amino acid), each peptide may have a longer peptide chain by having additional amino acids added to the terminal portion of each. These additional amino acids may be ones that flank the peptides in the apo(a) molecule (provided the peptide does not extend to a point in the apo(a) molecule where repeated epitopes reside), or they may be heterologous amino acids. Analogues have substantially the same amino acid residues as do each of SEQ ID NOS:2, 4, 6, 8, 10, 12, 14, 16, 18, 20, 22, 24, 26, 28, 30, 32, 34, 36, 38 and 40, but with some amino acids being conservatively substituted while the peptides retain the defined reactivity to anti-apo(a) monoclonal antibodies, are also considered as part of this invention.

Significantly, all of the peptides of the present invention contain non-repetitive epitopes of the apo(a) molecule, do not occur in the plasminogen molecule, and could be used to raise antibodies that would recognize all isoforms of apo(a) on an equivalent molar basis. Because of all of these properties, the antibodies raised against these peptides can be used in an immunoassay to quantitatively detect apo(a).

The isolation and detection of the peptides of the present invention began by isolating Lp(a) from freshly obtained human plasma by sequential isopycnic ultracentrifugation. The Lp(a) fraction was purified by gel filtration chromatography and dialyzed. Anti-apo(a) monoclonal antibodies were raised, using a modification of the method of Butman et al. (Appl. Environ Microbiol., 54:1564–69 (1988)).

Figure 3A:
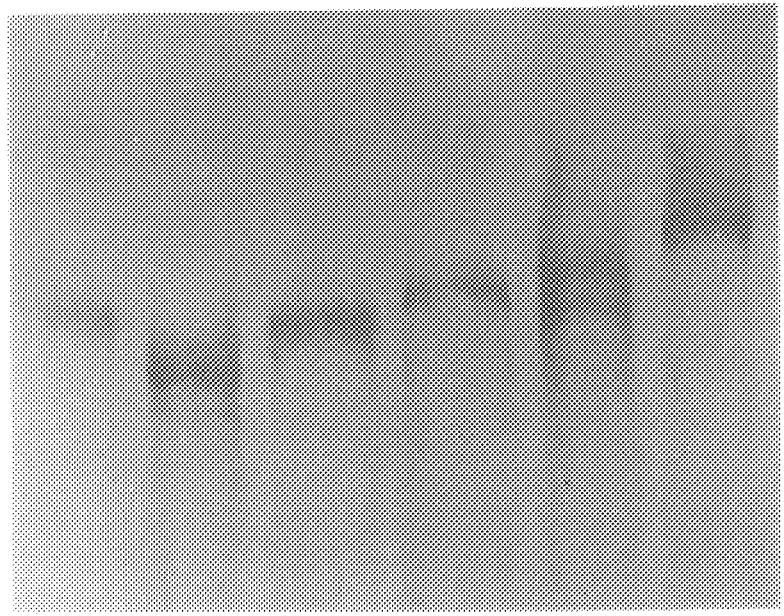
FIGS. 3A and 3B are the Western blot analysis of human (A) and rhesus monkey (B) apo(a) in plasma after SDS-PAGE under reducing conditions. Samples from both species were reacted against the anti-apo(a) monoclonal antibody 2D1.
Figure 3B:
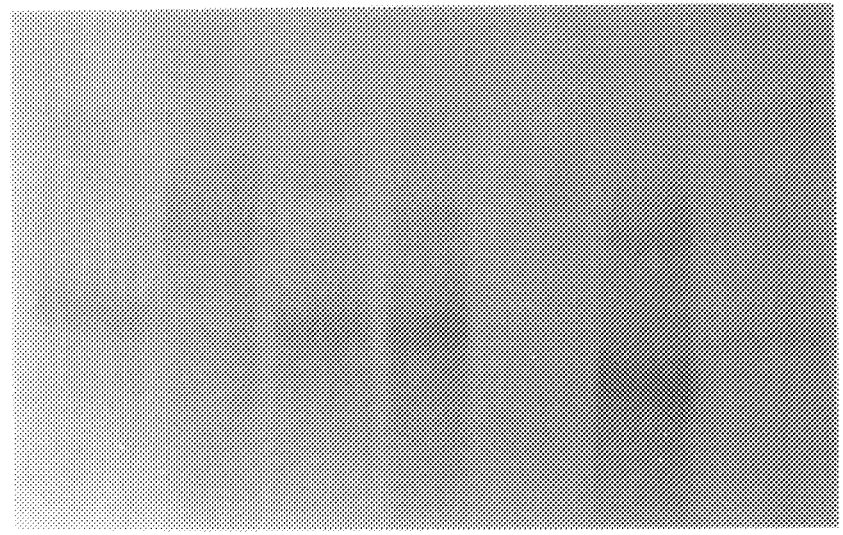
Figures 5A, 5B, 5C:
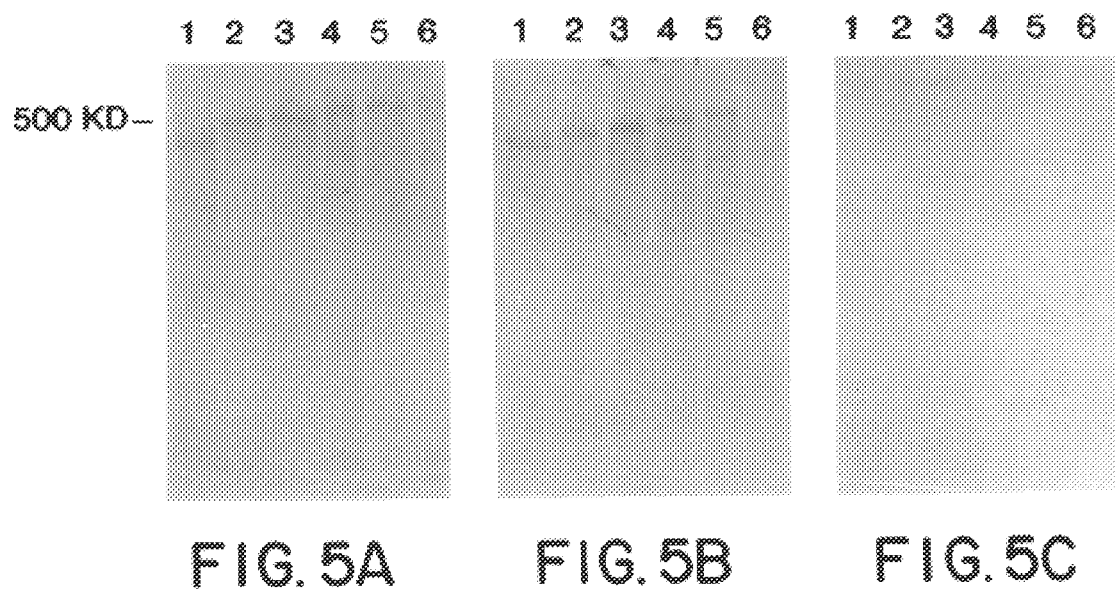
FIGS. 5A–C show a comparison of monoclonal antibodies reactive with denatured and reduced apo(a) by Western blot.

Two IgG$_1$ Mab cell lines, 2D1 and 12C11, were obtained after screening hybridoma supernates that reacted with Lp(a) but not with plasminogen or LDL. Both 2D1 and 12C11 were evaluated for specificity by Western blot analysis. Sera from several species, including human, rhesus monkey, dog, cat, rabbit and rat, of which only human and monkey reportedly contain Lp(a), were subjected to agarose gel electrophoresis, transferred to nitrocellulose, and then probed with 2D1 and 12C11. Mab 2D1 reacted with both rhesus monkey and human Lp(a) while Mab 12C11 reacted only with human Lp(a). Both Mab 2D1 and 12C11 were then used to probe blots of human and rhesus monkey serum subjected to SDS-PAGE under reducing conditions and transferred to nitrocellulose. 2D1 reacted with human apo(a) isoforms ranging from 300 kD to 800 kD and could distinguish several different rhesus monkey apo(a) isoforms, as shown in FIGS. 3A and B. In FIG. 3, the top Western blot (A) of human apo(a) in plasma samples where lane 1 is the apo B-100 control, lane 2 is the apo(a) F isoform, lane 3 is the apo(a) B isoform, lane 4 is the apo(a) S1 isoform, lane 5 is the apo(a) S1 and S2 isoforms and lane 6 the apo(a) S3 isoform. The bottom (B) Western blot is of rhesus monkey apo(a) in plasma samples, where lane 1 is human apo B-100 control, and lanes 2–7 are different rhesus monkey plasma samples. Additionally, 2D1 reacted with baboon, African green and cynomologous monkey apo(a) using this method. 12C11 did not react with reduced, denatured Lp(a) from either species, but did react with all isoforms of native Lp(a) from agarose gels, as shown in FIGS. 4A–D and 5A–C.

FIGS. 4(A–D) shows the agarose gel electrophoresis and Western blot analysis of isolated lipoproteins. Lipoprotein fractions were subjected to native agarose gel electrophoresis. One-half of the gel was stained with Fat Red 7B for lipids (C and D). Proteins from the other half (A and B) were transferred to nitrocellulose and probed with either 2D1 (left side) or 12C11 (right side) and developed. The lanes are: 1) pooled lipoprotein-deficient plasma (>1.21 g/ml), 2) HDL/Lp(a) (1.063–1.21 g/ml), 3) LDL (1.03–1.05 g/ml), and 4) VLDL (1.006–1.019 g/ml).

FIG. 5(A–C) is a comparison of antibody reactivity with denatured/reduced apo(a) by Western blot analysis. Plasma samples were subjected to SDS-PAGE (3% stacking, 5% running gel) under reducing conditions. Proteins were transferred to nitrocellulose, probed with Mabs to apo(a): A) clone 4F3, B) clone 2D1, and C) clone 12C11 and developed. Lanes are: 1) apo(a) F isoform, 2) apo(a) B isoform, 3) apo(a) S1 isoform, 4) apo(a) S2 isoform, 5) apo(a) S3 isoform, and 6) apo(a) S4 isoform.

Both 2D1 and 12C11 were evaluated as capture antibodies, using HRP-labeled polyclonal anti-apo B antibody as the conjugate. No significant differences were seen between the two antibodies in their ability to capture the different human apo(a) isoforms of purified Lp(a) or Lp(a) in plasma samples when coated at their optimal concentration. To determine whether 2D1 and 12C11 reacted with a repeated epitope, both antibodies were conjugated to HRP and then used as detection antibodies in a sandwich ELISA.

Figure 6:
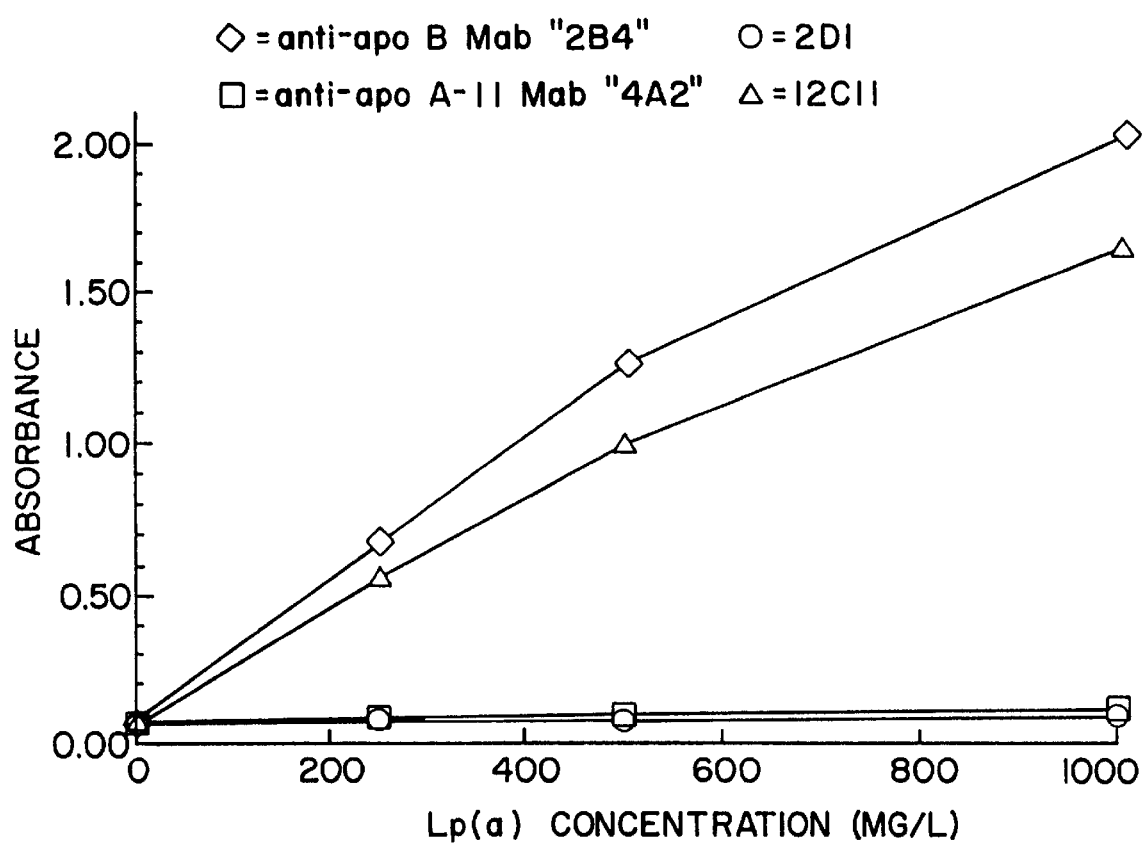
FIG. 6 is the binding analysis of monoclonal antibody 2D1.

Microtiter plate wells were first coated with various Mab against either apo(a) (2D1, 12C11), apo B100 (Mab 2B4), or an irrelevant lipoprotein antigen, apo A-II (Mab 4A2). The ELISA was performed as described above, with Lp(a) in plasma as the antigen. HRP-labeled 2D1 bound to Lp(a) captured by either the solid phase 12C11 or 2B4, but did not bind to Lp(a) captured by itself, as shown in FIG. 6. The experiment depicted in FIG. 6 was performed as follows: blocked microtiter plates were coated with 10 mg/L 2D1, 12C11, an anti-apo B Mab (2B4) or an anti-apo A-II Mab (4A2). Known concentrations of the Lp(a) plasma calibrator (0, 250, 500 and 1000 mg/L) were added, incubated and then washed. Mab 2D1 conjugated to HRP (1 mg/L, 100 microliters) was added and incubated for 1 hour at 37° C. Wells were washed and color developed with TMB substrate. The results are shown in FIG. 6.

On the other hand, HRP-labeled 12C11 could bind to Lp(a) captured not only by solid phase 2D1 and 2B4 but also by 12C11 itself. These results suggested that 12C11, but not 2D1, recognized a repeating epitope. Based on the above findings, in addition to its interesting reaction with Old World monkey Lp(a), 2D1 was chosen as the capture monoclonal antibody for the APO-TEK Lp(a) ELISA Test System (Trademark of Organon Teknika Corporation, Durham, N.C., USA.)

Epitope mapping studies were undertaken to confirm the above findings and determine the amino acid sequence of the epitope. Because 2D1 recognized a non-repetitive epitope in apo(a), focus was placed on non-repetitive regions in the carboxyl terminal region of the molecule. Approximately 70% of the apo(a) molecule can be considered to be highly repetitive in nature, which contains segments A and B. Furthermore, other Kringle IV-like domains, #1 and #30–37, though not identical to the highly repeated Kringle IV-like domains, are extremely similar to the A and B domains. These extensive similarities suggested that the unique epitope of 2D1 was much less likely to be in this region than the protease or Kringle 5 regions. However, since rhesus monkey apo(a) does not contain the Kringle 5 domain, the most likely location of the epitope was in the protease-like domain.

Figure 2:
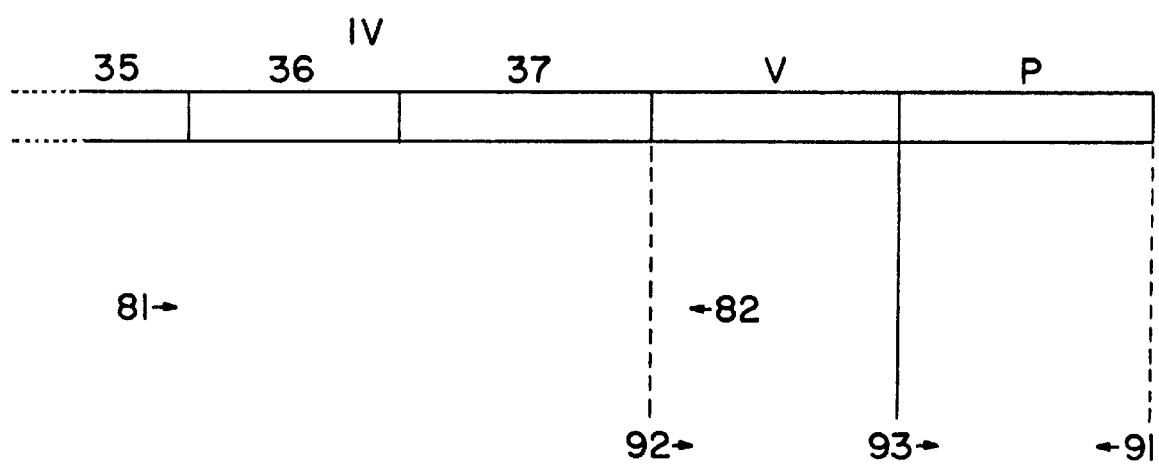
FIG. 2 is the carboxyl terminal map of apo(a).

The well known polymerase chain reaction ("PCR") was used to amplify the gene segment of interest, as shown in FIG. 2 and to create BamHI restriction sites flanking the fragment which are appropriate for cloning. The amplification reactions produced unique DNA fragments of the appropriate size, 950 bp for the Kringle 5 domain, which contains a large sequence of the Kringle 4 domains (part of the 35th and all of the 36th and 37th kringle 4 domains) ("35-V"), 700 bp for the protease domain ("P"), and 1000 bp for the Kringle 5/protease domains combined ("V+P"). As shown in FIG. 2, the oligonucleotide primer pairs designed for amplification were designed as follows: 1) 35-V, pairs 81 and 82, 2) V+P, pairs 92 and 91, and 3) P, pairs 93 and 91.

Figure 7A:
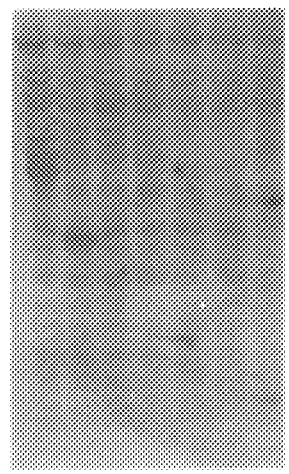
FIGS. 7A and B show the Western blot analysis of recombinant proteins after SDS-PAGE under reducing conditions, transferred and probed with antibodies against Lp(a) and apo(a).
Figure 7B:
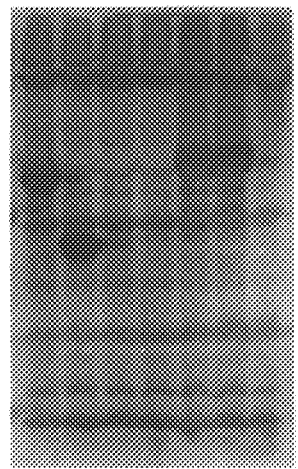

The fragments were cloned into the pET 11a expression plasmid. Clones which expressed the appropriate sized protein (approximately 35 kD for 35-V, 24 kD for P and 36 kD for V+P) were tested for reactivity to 2D1 and to a positive control, a polyclonal antibody against Lp(a), by Western blot analysis, as shown in FIG. 7(A–B). The lanes, in FIG. 7(A–B), are 1) V+P, 2) P, 3) and 4) non-expressed recombinant protein, 5) 35-V clone 1, 6) 35 -V, clone 2 and 7) a negative control for a highly expressed irrelevant protein. The Mab 2D1 recognized only the polypeptide which represents the protease domain alone (amino acids 4309–4529). This was not surprising since it was known that 2D1 reacts with rhesus monkey apo(a), which does not contain a Kringle 5 domain, and also did not react with a repetitive epitope (i.e., Kringle 4 domains). As expected, the polyclonal antibody recognized all polypeptides containing apolipoprotein(a) sequences. Binding of 2D1 was not a non-specific association to a large amount of protein because it did not bind to the 35-V peptide at all. Therefore, the epitope recognized by the Mab 2D1 is within the non-repeated protease-like region of the apolipoprotein(a) molecule.

To further define the epitope that reacts with Mab 2D1, the so-called PEPSCAN method was employed. Briefly, the entire amino acid sequence of the protease domain of apo(a) was used to generate 12-mer peptides beginning at each position along the protease domain. Each one of these peptides was allowed to react with 2D1 in a liquid/liquid type of hybridization, and a positive reaction was detected by a colorimetric reaction. By this method, it was determined that the epitope for 2D1 is contained in an 11-mer peptide having the sequence of SEQ ID NO:2.

Since 2D1 reacts with all Old World monkey apo(a) and human apo(a), but not human or Old World monkey plasminogen, the amino acid sequences as shown in FIG. 8 were compared and about 8 additional non-repetitive sequences of amino acids, common to the Old World monkeys and humans, but not plasminogen, were found:

TARTECYITGWGE (SEQ ID NO:4)
PDYMVTARTECYI (SEQ ID NO:6)
KKCPGSIVGGCVA (SEQ ID NO:8)

LRTRFGKHFCGGT (SEQ ID NO:10)
HCLKKSSRPSSYK (SEQ ID NO:12)
QEVNLESHVQEIE (SEQ ID NO:14)
ALLKLSRPAVITD (SEQ ID NO:16)
ENEVCNHYKYICA (SEQ ID NO:18)

One way to determine if antibodies raised or developed against these peptides (or appropriate fragments thereof) would react with the native apo(a), is to use Dot Blot analysis in which the different isoforms of apo(a) are reconstituted in phosphate buffered saline ("PBS"), applied to a nitrocellulose membrane at several concentrations, allowed to dry, then probed with the antibodies after blocking. Antibodies giving a positive reaction, especially to all of the isoforms, would be useful in quantitative immunoassays of test samples.

The peptides of the present invention may be synthesized by standard chemical synthetic techniques, such as the Merrifield technique, or through recombinant nucleic acid techniques as described above, where the peptides are finally expressed in a suitable microorganism.

The organic chemical methods for peptide synthesis include coupling of the required amino acids by means of a condensation reaction, either in homogeneous phase or with the aid of a solid phase.

The condensation reaction can be carried out as follows:
a) condensation of a compound (amino acid, peptide) with a free carboxyl group and protected other reactive groups with a compound (amino acid, peptide) with a free amino group and protected other reactive groups, where one of the protecting groups also may be a (derivatized) solid support, in the presence of a condensation agent;
b) condensation of a compound (amino acid, peptide) with an activated carboxyl group and free or protected other reaction groups with a compound (amino acid, peptide) with a free amino group and free or protected other reactive groups, where one of the protecting groups also may be a (derivatized) solid support.

Activation of the carboxyl group can take place, for example, by converting the carboxyl group to an acid halide, azide, anhydride, imidazolide or an activated ester, such as the N-hydroxy-succinimide, N-hydroxy-benzotriazole, p-nitrophenyl, 3,4-dihydro-3-hydroxy-4-oxo-1,2,3-benzotriazine (ODhbt) or pentafluorophenyl (OPfp) ester.

The most common methods for the above condensation reactions are: the carbodiimide method, the BOP method [benzotriazolyl-oxytris (dimethyl-amino) phosphonium hexafluoro phosphate], the TBTU method [2-(1H-benzotriazol-1-yl)-1,1,3,3-tetramethyluronium tetrafluoroborate, the azide method, the mixed anhydride method and the method using activated esters, such as described in The Peptides, Analysis, Synthesis, Biology Vol. 1–3 (Ed. Gross, E. and Meienhofer, J.) 1979, 1980, and 1081 (Academic Press, Inc.).

Particularly suitable solid phases are, for example, the p-alkoxybenzyl alcohol resin (4-hydroxy-methyl-, phenoxy-methyl-copolystrene-1% divinylbenzene resin), described by Wang (1974) J. Am. Chem. Soc. 95, 1328 and similarly functionalized co-polymers of N,N-dimethylacrylamide, acryloylsarcosine methylester and bisacryloylethylenediamine supported by a matrix of an inert macroporous kieselguhr described by Atherton (1981) J. Chem. Soc., Chem. Comm. 1151. After synthesis the peptides can be split from this solid phase under mild conditions. Other suitable supports are derivatized cross-linked polystyrene, polyethylene or polypropylene rods as described by Geysen, P.N.A.S., 81, 3998 (1984) and P.N.A.S. 82, 178 (1985).

Once the peptides are synthesized and purified, they can be used as immunogens, when conjugated to a larger molecule, such as bovine serum albumin. Once conjugated and using suitable and well known methods, they can be introduced into an animal such as a mouse, rat or rabbit, and antibodies to these conjugated peptides will be produced. Monoclonal or polyclonal antibodies can be developed from the immunized animals using well known methods. See *Antibodies: A laboratory manual*, supra, incorporated herein by reference.

These peptides, when purified, are also useful in an immunoassay designed to detect or quantitate the presence of apo(a) in a test sample. The test sample usually is a serum or plasma sample. For instance, in a competitive inhibition immunoassay, unlabeled anti-apo(a) antibodies (raised to be reactive with a peptide of the present invention) are bound to a solid phase or a solid support, such as the walls of a microtiter well, a plastic support, such as a dip-stick, or beads made from any number of materials such as latex, silica, ceramic materials and metals. Purified peptides are labeled in any of a number of ways, for example, with HRP, radioisotopes, gold sol, alkaline phosphatase, or other enzymes detectable upon the addition of substrate, and fluorescent chemicals such as fluorescein and rhodamine. These labeled peptides are mixed with the test sample containing an unknown amount of the antigen, apo(a). This mixture is added to the bound anti-apo(a) antibody. The antigen in the test sample competes with the labeled apo(a) peptides for binding to the bound antibody. The solid phase is incubated and washed, the labeled peptide is detected, and apo(a) in the test sample can then be determined or quantitated.

Antibodies (monoclonal or polyclonal) that are reactive with the peptides of the present invention and that have been raised or developed using the peptides can also be used in immunoassays for apo(a). For instance, the antibody can be used in a sandwich ELISA and function as the capture antibody and as the detection antibody (appropriately labelled with labels known in the art, see *Antibodies: A laboratory manual*, supra, incorporated herein by reference); alternatively, the antibody can be the capture antibody and an anti-apo B-peroxidase conjugate can act as the detection antibody. Methods for performing sandwich ELISAs are known in the art and the present invention is not intended to be limited to any particular immunoassay.

The invention also consists of the fragments of the DNA that code for the peptides comprising the sequences of SEQ ID NOS:2, 4, 6, 8, 10, 12, 14, 16, 18, 20, 22, 24, 26, 28, 30, 32, 34, 36, 38 and 40 and immunologically reactive fragments thereof, and their complementary (antisense) strands. The nucleotide sequences also included are those variants that have had replacements of bases due to the degeneracy of the nucleic acid code or to mutations, but will code for the peptides as described.

These nucleotide sequences may be synthesized by chemical or recombinant methods well known to those skilled in the art. The oligonucleotides so synthesized can be used as primers or as probes when labeled as described above, or can be inserted into appropriate expression vectors to recombinantly produce the peptides. These primers or probes can be used in assays to detect sequences amplified by either NASBA, PCR or other amplification technologies to detect or quantitate apo(a) nucleic acids. As stated previously, this segment of the apo(a) molecule is a unique segment of the molecule found in all human and old World monkey species isoforms because it is a highly conserved region of the gene. This conservation is of particular importance as the same reagents, such as the probes and primers described above, can be developed to detect apo(a) in both humans and in Old World monkeys, a model system for atherogenesis. The sequences of some of the DNA fragments included in the scope of the present invention are:

TTC TTG GAG CCC ACA CAA GCA GAT ATT GCC TTG (SEQ ID NO:1)
ACC GCC AGG ACT GAA TGT TAC ATC ACT GGC TGG GGA GAA (SEQ. ID NO:3)
CCA GAC TAC ATG GTC ACC GCC AGG ACT GAA TGT TAC ATC (SEQ ID NO:5)
AAG AAA TGT CCT GGA AGC ATT GTA GGG GGG TGT GTG GCC (SEQ ID NO:7)
CTC AGA ACA AGG TTT GGA AAG CAC TTC TGT GGA GGC ACC (SEQ ID NO:9)
CAC TGC TTG AAG AAG TCC TCA AGG CCT TCA TCC TAC AAG (SEQ ID NO:11)
CAA GAA GTG AAC CTC GAA TCT CAT GTT CAG GAA ATA GAA (SEQ ID NO:13)
GCC TTG CTA AAG CTA AGC AGG CCT GCC GTC ATC ACT GAC (SEQ ID NO:15)
GAG AAT GAA GTG TGC AAT CAC TAT AAG TAT ATT TGT GCT (SEQ ID NO:17)
CTG TTC TTG GAG CCC ACA CAA GCA GAT ATT GCC TTG (SEQ ID NO:19)
TTC TTG GAG CCC ACA CAA GCA GAT ATT GCC TTG CTA (SEQ ID NO:21)
CCC ACA CAA GCA GAT (SEQ ID NO:23)
GAA TGT TAC ATC ACT (SEQ ID NO:25)
GTC ACC GCC AGG ACT (SEQ ID NO:27)
GGA AGC ATT GTA GGG (SEQ ID NO:29)
TTT GGA AAC CAC TTC (SEQ ID NO:31)
AAG TCC TCA AGG CCT (SEQ ID NO:33)
CTC GAA TCT CAT GTT (SEQ ID NO:35)
CTA AGC AGG CCT GCC (SEQ ID NO:37)
TGC AAT CAC TAT AAG (SEQ ID NO:39)

Due to the degeneracy of the genetic code, any oligonucleotide that would code for any of the peptides of SEQ ID NOS: 2, 4, 6, 8, 10, 12, 14, 16, 18, 20, 22, 24, 26, 28, 30, 32, 34, 36, 38 and 40 is also envisioned as part of the invention, as is the complementary oligonucleotide for each of the above DNA fragments. In addition, nucleic acid sequences that code for immunologically active fragments of the peptides are contemplated as being part of the present invention.

The peptides, nucleic acids and antibodies of the invention can be packaged and sold in kit form. A kit can consist of individual containers with various reagents needed to perform the assay of interest. For example, a competitive inhibition immunoassay kit to detect apo(a) could consist of a solid phase such as a microtiter plate or a dipstick coated with an anti-apo(a) antibody and a container with at least one peptide of the invention that may be labeled as described previously herein. A kit to be used in conjunction with amplification technology could contain a container with a nucleic acid probe of the invention that may be labeled as described in the art or a separate container of material to be used for labeling. Still another kit that could be used for performing a sandwich ELISA may contain a container with a monoclonal or polyclonal antibody preparation or a solid phase, such as a dipstick or a microtiter plate, which is coated with the antibody(ies). Other individual containers, for any type of kit, could contain standard or control substances, buffers or water. For instance, the controls may comprise a low Lp(a)/apo(a) level control serum and a high Lp(a)/apo(a) level control serum to indicate whether or not the assay is performing properly. The individual containers would then be packaged in an outer container, such as a box, and sold as a kit that can be used to detect apo(a).

The following examples are given to further describe, but not limit the invention.

EXAMPLE 1

Isolation of Lp(a)

Lp(a) was isolated from freshly obtained human plasma containing EDTA by sequential isopycnic ultracentrifugation at the density range of 1.063 to 1.21 kg/L; potassium bromide was used to adjust the density. For production of monoclonal antibodies, the Lp(a) fraction was then purified by gel filtration chromatography and dialyzed against 150 mmol/L NaCl containing EDTA, 0.1 g/L.

EXAMPLE 2

Production and Purification of Monoclonal Antibody to apo(a)

Apo(a)-specific hybridomas were generated. Eight-week-old Balb/c female mice (Simonsen Laboratories, Gilroy, CA) were immunized subcutaneously with 100 µg of purified Lp(a) in complete Freund's adjuvant and boosted subcutaneously on days 14, 28, 56, and 105 with 100 µg of purified Lp(a) in PBS. Mice were then boosted at week 16 for three consecutive days with 10 µg of purified Lp(a) in PBS both intravenously and intraperitoneally; splenocytes obtained on the fourth day were used for fusions. Antibody-producing hypoxanthine-aminopterine-thymidine-resistant hybrids were screened by sandwich ELISA against purified Lp(a), LDL, and plasminogen (Enzyme Research Laboratories, Inc., South Bend, Ind., USA) and were cloned twice by limiting dilution. Mab, including 2D1 and 12C11, purified from ascitic fluid by use of Protein A-Sepharose chromatography, were isotyped by double immunodiffusion. Both of the monoclonal antibodies are $IgG_1$.

EXAMPLE 3

Electrophoretic Methods

These methods were used to detect apo(a) and fragments thereof.

Sodium dodecyl sulfate-polyacrylamide gel electrophoresis (SDS-PAGE) was performed in a 3% stacking gel at pH 6.8 and a 5% running gel at pH 8.8. Plasma samples were diluted in an equal volume of sample buffer consisting of, per liter, 125 mmol of Tris·HCl, pH 6.8, 402 g of sodium dodecyl sulfate (SDS), 200 mL of glycerol, 100 mL of 2-mercaptoethanol, and 50 mg of bromphenol blue and then were boiled for 5 min. Electrophoresis was performed at a constant voltage of 100 V until the samples entered the running gel and 180 V thereafter until the dye front had run off the gel. Proteins were electrophoretically transferred from the gel to a 0.45-µm-pore-size nitrocellulose membrane in a buffer (per liter) of 25 mmol of Tris, 192 mmol of glycine, pH 8.3, and 200 mL of methanol. Electrophoretic transfer was carried out at a constant voltage of 30 V for 24h at 10° C.

Agarose gel electrophoresis was performed using the Electrophoresis System of Ciba-Corning Diagnostics Corporation, Palo Alto, Calif., USA, according to the manufacturer's instructions to assess reactivity of anti-apo(a) Mab to native Lp(a). Separated lipoprotein classes were then transferred to 0.45 μm nitrocellulose by passive diffusion for 4h at room temperature.

Production of the desired recombinant protein was determined by visualizing protein products of induced cell cultures. Insert-containing clones were cultured until the $OD_{600}$ reached approximately 1, then isopropylthiogalactoside (IPTG) was added to a final concentration of 1 mM. After 1 to 2 hours, samples were removed for analysis. Samples were analyzed by SDS-PAGE using the mini-gel system of Novex Company (San Diego, Calif.). For the larger polypeptides (e.g., Kringle 5 and protease regions), a 12% resolving gel was employed. Preparation and electrophoresis of gels were done according to the manufacturer's, Novex, recommendations. Protein was detected by using Coomassie Brilliant blue stain (Sigma, St. Louis, Mo.). The transfer of the fractionated proteins was performed using the Novex transfer apparatus as directed by the manufacturer, Novex.

Based on this experiment, it was determined which clones expressed the desired peptides for use in further analysis.

EXAMPLE 4

Western Blot Analysis of apo(a) Isoforms and Cloned apo(a) Sequences

To identify apo(a) isoforms in plasma and to confirm specificity of anti-apo(a) Mab, the nitrocellulose membranes, containing the electrophoretically transferred proteins after SDS-PAGE or agarose gel electrophoresis, were blocked with "Blotto", which is Dulbecco's modified PBS containing dry milk, 50 g/L for 1h at 37° C. and then washed with PBS five times over a period of 20 min with shaking. The membranes were incubated overnight at 4° C. with mouse anti-human apo(a), clone 2D1, 10 μg/mL diluted in 100 mmol/L Tris·HCl, 150 mmol/L NaCl, pH 7.2 containing bovine serum albumin, 10 g/L. The blot was washed as before with PBS containing Tween 20 (0.5 mL/L) and then incubated with HRP-labeled goat anti-mouse IgG, A, and M (Hyclone) diluted to 0.5 mg/L in Blotto containing goat serum, 100 mL/L, for 1h at 37° C. The membrane was washed as before with PBS containing Tween 20, 0.5 mL/L. The blot was then developed with a solution of 0.6 g of diamino-benzidine (DAB), 0.6 g of $CoCl_2$, and 3.0 ml of $H_2O_2$ per liter of PBS for 2 to 5 min at room temperature. The reaction was terminated with deionized $H_2O$.

In some cases a rabbit anti-human Lp(a) antiserum (Behringwerke AG, Marburg, Germany) was used as the primary antibody (diluted 1:500 in Blotto). After washing, the blot was incubated with HRP-labeled goat anti-rabbit IgG (KPL, Gaithersburg, Md.) diluted to 2 mg/L in Blotto.

To determine the electrophoretic mobility relative to apo B-100, we incubated a strip from each blot with HRP-labeled sheep anti-human apo B (Biodesign, Kennebunkport, Me., USA) 5 μg/mL, overnight at 4° C. after blocking, and developed the result as described. Apo(a) isoforms were assigned according to the method of Utermann et al. as described above.

The results of the Western blots are shown in FIGS. 3(A and B), 4(A–D), 5(A–C), and 7(A and B).

EXAMPLE 5

Lp(a) sandwich ELISA

Wells of flat-bottomed micro ELISA plates were coated with Mab 2D1 (10 μg/mL) by incubating overnight at 4° C.

in 0.05 mol/L sodium bicarbonate buffer, pH 9.6. After removing the coating buffer, 300 μL of blocking buffer was added and incubated for 1h at room temperature. Plasma calibrators were diluted in sample diluent to the working range of concentrations (6.25 to 200 μg/L). Plasma samples and calibrated controls were diluted 5000-fold in sample diluent. Calibrators, controls, and samples (100 μL) were added to blocked wells and incubated for 1h at 37° C. The wells were washed five times with 300 μL of a wash buffer of 10 mL of glycerol and 0.5 mL of Tween 20 per liter. After washing, 100 μL of HRP-labeled sheep anti-human apo B (Organon Teknika/Biotechnology Research Institute, Rockville, Md.) diluted 5000-fold in conjugate diluent (Medix Biotech, Foster City, Calif.) was added to each well and incubated for 1h at 37° C. Wells were washed, and color development was achieved with TMB. A standard curve was generated by plotting the absorbance at 450 nm versus Lp(a) concentration by linear regression. Values for sample concentrations were obtained by interpolating their absorbance from the standard curve. MAb 2D1 and 12C11 performed equally well as capture antibodies. However, only 2D1 recognized old World monkey apo(a) and could therefore be used to quantitate Lp(a) in these species.

To determine binding characteristics of 2D1, microtiter plates were coated with 10 μg/ml 2D1 or another Mab. To the plates, known concentrations of Lp(a) plasma calibrator (0, 250, 500, or 1000 mg/L) were added, incubated, and then washed as described above. Mab 2D1 conjugated to HRP (1 μg/ml, 100 μL) was added and incubated for 1 hour at 37° C. Wells were washed and developed as described above.

Mab 2D1 recognizes a non-repetitive epitope, whereas 12C11 recognizes a repeating, or different, epitope. FIG. 6 shows the binding affinity of 2D1.

EXAMPLE 6

Conjuqation of Mab to HRP

Using standard techniques, Mab 2D1 and 12C11 were labeled with HRP at a molar ratio of 1:7 of IgG:HRP.

EXAMPLE 7

Preparation of cDNA Template cDNA was prepared from 5 μg normal human liver RNA (Clonetech, Palo Alto, Calif.) using the cDNA synthesis system of Promega (Madison, Wis.), according to manufacturer's instructions, except that random primers were used rather than oligo dT. The cDNA so prepared was used in later PCR amplification.

EXAMPLE 8

Amplification of DNA Segments

PCR amplification reactions (50–100 μl total volume) were performed using 1–3 μl of the cDNA template produced in Example 7, 100 μg of each primer described below, essentially according to the supplier Perkin-Elmer (Norwalk, Conn.). The cycling parameters were: 94° C., 4' one cycle and 94° C., 1'; 50° C., 1'; 72° C., 1' for thirty cycles. Amplified DNA products were analyzed according to standard techniques and found to be in sufficient quantity for cloning.

Primer oligonucleotides for carboxyl terminal mapping (see FIG. 2 :

81: AGCTAGGAAT CCGAATCGAG TGTCCTCACA ACT (SEQ ID NO:41)

82: AGCTAGGGAT CCATTCATTG TGTAGCACCA
GGGACC (SEQ ID NO:42)t

91: AGCTAGGGAT CCGTAGGTTG ATGCTTCACT
CTG (SEQ ID NO:43)

92: AGCTAGGGAT CCCAAGACTG TATGTTTGGG
AAT (SEQ ID NO:44)

93: AGCTAGGGAT CCATTGTAGG GGCGTGTGTG
GCC (SEQ ID NO:45)

EXAMPLE 9

Cloning of apo (a) Fragments

Cloning experiments were performed according to established procedures. Amplified DNA fragments and the cloning vector pET 11a (Novagen, Madison, Wis.) were cleaved using BamHI. Following dephosphorylation of the vector using alkaline phosphatase the vector and insert were ligated. Competent BL21(DE3) E. coli cells (Novagen, Madison, Wis.) were transformed using the ligation product.

EXAMPLE 10

PEPSCAN analysis of protease domain

The protease domain as depicted in FIG. 7 was analyzed using the PEPSCAN method. 12-mer peptides, beginning at each position along the protease domain molecule were synthesized. Each one of these 12-mer peptides were reacted first with the 2D1 antibody (1/100 dilution) in a liquid/liquid hybridization system. In order to detect binding of 2D1 to the 12-mer, a second antibody directed against the 2D1, rat anti-mouse antibody labelled with peroxidase, was then added to the reaction mixture. A positive result was indicated by a calorimetric reaction. The results showed two 12-mers (SEQ ID NO:20 and 22), that bound to 2D1 antibody and produced a relative absorbance value of about 10×higher than the other 12-mers synthesized along this protease domain. Since both of these peptides reacted equally strong, it can be concluded that the epitope for 2D1 is the 11 amino acid sequence peptide given when these two peptides are overlapped; i.e., the peptide of SEQ ID NO:2.

We claim:

1. An antibody that reacts with human and Old World monkey apo(a), apolipoprotein(a) but not with human and Old World monkey plasminogen, and which specifically binds to a peptide having an amino acid sequence selected from the group consisting of SEQ ID NO:4, SEQ ID NO:6, SEQ ID NO:8, SEQ ID NO:10, SEQ ID NO:12, SEQ ID NO:14, SEQ ID NO:16, and SEQ ID NO:18.

2. An antibody that reacts with human and Old World monkey apo(a) but not with human and Old World monkey plasminogen, and which specifically binds to a peptide having an amino acid sequence selected from the group consisting of SEQ ID NO:26, SEQ ID NO:28, SEQ ID NO:30, SEQ ID NO:32, SEQ ID NO:34, SEQ ID NO:36, SEQ ID NO:38 and SEQ ID NO:40.

3. The antibody of claim 1, which is monoclonal.

4. The antibody of claim 2, which is monoclonal.

* * * * *